(12) United States Patent
Richardson et al.

(10) Patent No.: US 9,512,485 B2
(45) Date of Patent: Dec. 6, 2016

(54) METHODS FOR PREDICTING ANTI-CANCER RESPONSE

(75) Inventors: Andrea L. Richardson, Chestnut Hill, MA (US); Zhigang C. Wang, Newton, MA (US); Daniel P. Silver, Wayland, MA (US); Zoltan Szallasi, Boston, MA (US); Nicolai Juul Birkbak, Copenhagen (DK); Aron Charles Eklund, Copenhagen (DK)

(73) Assignees: Dana-Farber Cancer Institute. Inc., Boston, MA (US); The Brigham and Women's Hospital. Inc., Boston, MA (US); Children's Medical Center Corporation, Boston, MA (US); The Technical University of Denmark, Lyngby (DK)

( * ) Notice: Subject to any disclaimer, the term of this patent is extended or adjusted under 35 U.S.C. 154(b) by 718 days.

(21) Appl. No.: 13/818,425

(22) PCT Filed: Aug. 19, 2011

(86) PCT No.: PCT/US2011/048427
§ 371 (c)(1),
(2), (4) Date: Jul. 8, 2013

(87) PCT Pub. No.: WO2012/027224
PCT Pub. Date: Mar. 1, 2012

(65) Prior Publication Data
US 2013/0281312 A1 Oct. 24, 2013

Related U.S. Application Data

(60) Provisional application No. 61/402,116, filed on Aug. 24, 2010.

(51) Int. Cl.
*C12Q 1/68* (2006.01)
*C12P 19/34* (2006.01)
*A61K 38/00* (2006.01)
*C07D 487/00* (2006.01)

(52) U.S. Cl.
CPC ........ *C12Q 1/6886* (2013.01); *C12Q 2600/106* (2013.01); *C12Q 2600/118* (2013.01); *C12Q 2600/16* (2013.01)

(58) Field of Classification Search
CPC .............. C12Q 1/6886; C12Q 1/6874; C12Q 2600/156; G01N 2800/52; G01N 33/57415
See application file for complete search history.

(56) References Cited

U.S. PATENT DOCUMENTS

| | | | |
|---|---|---|---|
| 3,590,028 A | 6/1971 | Arcamone et al. |
| 3,892,790 A | 7/1975 | Tobe et al. |
| 3,904,663 A | 9/1975 | Tobe et al. |
| 4,138,480 A | 2/1979 | Gosalvez et al. |
| 4,946,954 A | 8/1990 | Talebian et al. |
| 4,950,738 A | 8/1990 | King et al. |
| 4,996,337 A | 2/1991 | Bitha et al. |
| 5,091,521 A | 2/1992 | Kolar et al. |
| 5,177,075 A | 1/1993 | Suto et al. |
| 5,295,944 A | 3/1994 | Teicher et al. |
| 5,434,256 A | 7/1995 | Khokhar et al. |
| 5,445,934 A | 8/1995 | Fodor et al. |
| 5,510,270 A | 4/1996 | Fodor et al. |
| 5,527,905 A | 6/1996 | Sugimura et al. |
| 5,539,083 A | 7/1996 | Cook et al. |
| 5,556,752 A | 9/1996 | Lockhart et al. |
| 5,578,832 A | 11/1996 | Trulson et al. |
| 5,633,016 A | 5/1997 | Johnson et al. |
| 5,633,243 A | 5/1997 | Sugimura et al. |
| 5,744,305 A | 4/1998 | Fodor et al. |
| RE36,397 E | 11/1999 | Zhang et al. |
| 6,040,138 A | 3/2000 | Lockhart et al. |
| 6,087,340 A | 7/2000 | Gatti et al. |
| 6,210,891 B1 | 4/2001 | Nyren et al. |
| 6,214,821 B1 | 4/2001 | Daoud |
| 6,258,568 B1 | 7/2001 | Nyren et al. |
| 6,274,320 B1 | 8/2001 | Rothberg et al. |
| 6,403,563 B1 | 6/2002 | Geroni et al. |
| 6,455,258 B2 | 9/2002 | Bastian et al. |
| 6,465,177 B1 | 10/2002 | Hoon |
| 6,534,293 B1 | 3/2003 | Barany et al. |
| 7,351,701 B2 | 4/2008 | Helleday et al. |
| 7,485,707 B2 | 2/2009 | Matvienko et al. |
| 7,732,491 B2 | 6/2010 | Sherman et al. |
| 7,754,684 B2 | 7/2010 | Stewart et al. |
| 7,759,488 B2 | 7/2010 | Xiao et al. |
| 7,759,510 B2 | 7/2010 | Kay et al. |
| 7,858,331 B2 | 12/2010 | D'Andrea et al. |

(Continued)

FOREIGN PATENT DOCUMENTS

| EP | 0430402 | 6/1991 |
|---|---|---|
| WO | 9841531 | 9/1998 |

(Continued)

OTHER PUBLICATIONS

Carr J. et al. Cancer Genetics and Cytogenetics 172 (2007) 127-138.*
De Preter et al. Cancer Letters 197 (2003) 53-61.*
Yaris N. et al. The Turkish Journal of Pediatrics 2004; 46: 182-185.*
Li C. et al. BMC Bioinformatics 2008, 9:204, pp. 1-16.*
Soule H.D. et al. Cancer Research, 50. 6075-6086. Sep. 15, 1990.*
Beder L B et al.: "Genome-wide analyses on loss of heterozygosity in head and neck squamous cell carcinomas", Laboratory Investigation, vol. 83, No. 1, 2003, pp. 99-105, XP002703165.
Buch H N et al.: "Prediction of recurrence of nonfunctioning pituitary tumours by loss of heterozygosity analysis", Clinical Endocrinology, vol. 61, 2004, p. 19-22, XP002703163.
Cheung T H et al.: "Clinicopathologic significance of loss of heterozygosity on chromosome 1 in cervical cancer" Gynecologic Oncology, Academic Press, London, GB, vol. 96, No. 2, Feb. 1, 2005 (Feb. 1, 2005), pp. 510-515, XP027205508, ISSN: 0090-8258 [retrieved on Jan. 18, 2005].

(Continued)

*Primary Examiner* — Stephen Kapushoc
(74) *Attorney, Agent, or Firm* — Nixon Peabody LLP; David S. Resnick; Leena H. Karttunen Contarino

(57) ABSTRACT

The present invention is based, in part, on the identification of novel methods for defining predictive biomarkers of response to anti-cancer drugs.

20 Claims, 8 Drawing Sheets

(56) References Cited

U.S. PATENT DOCUMENTS

| | | | |
|---|---|---|---|
| 7,868,040 | B2 | 1/2011 | Wilson et al. |
| 7,915,280 | B2 | 3/2011 | Ferraris et al. |
| 9,279,156 | B2 | 3/2016 | Gutin et al. |
| 2003/0049613 | A1 | 3/2003 | Perucho et al. |
| 2005/0112604 | A1 | 5/2005 | Fujimoto et al. |
| 2006/0088870 | A1 | 4/2006 | Finkelstein et al. |
| 2007/0004621 | A1 | 1/2007 | Shridhar et al. |
| 2007/0070349 | A1 | 3/2007 | Harris et al. |
| 2008/0108057 | A1 | 5/2008 | Griffith et al. |
| 2009/0081237 | A1 | 3/2009 | D'Andrea et al. |
| 2009/0246789 | A1 | 10/2009 | Buckhaults et al. |
| 2010/0145894 | A1 | 6/2010 | Semizarov et al. |
| 2010/0159466 | A1 | 6/2010 | Eng et al. |
| 2012/0015050 | A1 | 1/2012 | Abkevich et al. |
| 2013/0281312 | A1 | 10/2013 | Richardson et al. |
| 2015/0080260 | A1 | 3/2015 | Abkevich et al. |

FOREIGN PATENT DOCUMENTS

| | | | |
|---|---|---|---|
| WO | 9954498 | | 10/1999 |
| WO | 9520952 | | 11/1999 |
| WO | 0024933 | | 4/2000 |
| WO | 03074723 | | 9/2003 |
| WO | 2004042032 | A2 | 5/2004 |
| WO | 2006098978 | A1 | 9/2006 |
| WO | 2006/110855 | A2 | 10/2006 |
| WO | 2006/116341 | A1 | 11/2006 |
| WO | 2006128195 | | 11/2006 |
| WO | 2007035893 | | 3/2007 |
| WO | 2009033178 | | 3/2009 |
| WO | 2009/073869 | A1 | 6/2009 |
| WO | 2009148528 | A2 | 12/2009 |
| WO | 2010051318 | A2 | 5/2010 |
| WO | 2011048495 | A1 | 4/2011 |
| WO | 2011106541 | | 9/2011 |
| WO | 2011160063 | | 12/2011 |
| WO | 2012019000 | A2 | 2/2012 |
| WO | 2012027224 | | 3/2012 |
| WO | 2013/130347 | A1 | 9/2013 |
| WO | 2013182645 | | 12/2013 |

OTHER PUBLICATIONS

Extended European Search Report, from Application EP11748075.6, filed Jul. 29, 2013.

Feltmate C M et al.: "Whole-genome allelotyping identified distinct loss-of-heterozygosity patterns in mucinous ovarian and appendiceal carcinomas", Clinical Cancer Research, vol. 11, No. 21, Nov. 1, 2005 (Nov. 1, 2005), pp. 7651-7657, XP002703164.

Franko, J. et al., "Loss of heterozygosity predicts poor survival after resection of pancreatic adenocarcinoma," J. Gastrointest. Surg., Oct. 2008 vol. 12, No. 10, pp. 1664-1723.

Heinsohn, S. et al., "Determination of the prognostic value of loss of heterzygosity at the retinoblastoma gene in osteosarcoma," Int. J. Oncol., May 2007, vol. 30, No. 5, pp. 1205-1214.

Kerangueven, F. et al. Cancer Research 57, 5469-5475 (1997).

Medri, L. et al. modern Pathology 2003;16(11):1067-1075.

Murayama-Hosokawa, S. et al., "Genome-wide single-nucleotide polymorphism arrays in endometrial carcinomas associate extensive chromosomal instability with poor prognosis and unveil frequent chromosomal imbalances involved in the PI3-kinase pathway," Oncogene, Apr. 1, 2010, vol. 29, No. 13, pp. 1897-1908.

Ramirez, C. et al., "Loss of 1p, 19q, and 10q heterozygosity prospectively predicts prognosis of oligodendroglial tumors—towards individualized tumor treatment?" Neuro. Oncol., May 2010, vol. 12, No. 5, pp. 490-499.

Teh M-T et al.: "Genomewide Single Nucleotide Polymorphism Microarray Mapping in Basal Cell Carcinomas Unveils Uniparental Disomy as a Key Somatic Event", Cancer Research, vol. 65, No. 19, Oct. 1, 2005 (Oct. 1, 2005), pp. 8597-8603,XP002703167.

Tseng, R. C. et al., Genomewide loss of heterozygosity and its clinical associations in non-small cell lung cancer, Int. J. Cancer, Nov. 1, 2005, vol. 117, No. 2, pp. 241-247.

Valeri A et al.: "High frequency of allelic losses in high-grade prostate cancer is associated with biochemical progression after radical prostatctomy", Urologic Oncology, Elsevier, New York, NY, US, vol. 23, No. 2, Mar. 1, 2005 (Mar. 1, 2005), pp. 87-92, XP027799195, ISSN: 1078-1439 [retrieved on Mar. 1, 2005].

Pfeifer et al. "Genome-wide analysis of DNA copy number changes and LOH in CLL using high-density SNP arrays", BLOOD, vol. 109, No. 3, Oct. 5, 2006 (Oct. 5, 2006), pp. 1202-1210, XP055085782, ISSN: 0006-4971, DOI: 10.1182/blood-2006-07-034256 *abstract* *tables 2, 4*.

Popova et al. "Genome Alteration Print (GAP): a tool to visualize and mine complex cancer genomic profiles obtained by SNP arrays", Genome Biology, Biomed Central Ltd., London, GB, vol. 10, No. 11, Nov. 11, 2009 (Nov. 11, 2009), p. R128, XP021065372, ISSN: 1465-6906, DOI: 10.1186/GB-2009-10-11-R128.

Rakha et al. "Basal-like breast cancer: a critical review", Journal of Clinical Oncology, American Society of Clinical Oncology, US, vol. 26, No. 14, May 20, 2008 (May 20, 2008), pp. 2568-2581, XP002661082, ISSN:0732-183X, DOI: 10.1200/JCO.2007.13.1748.

Sakai et al.; Functional resoration of BRCA2 protein by secondary BRCA2 mutations in BRCA2-mutated ovarian carcinoma; Cancer Res; 2009, 69(16):6381-6386.

Sakai et al.; Secondary mutations as a mechanism of cisplatin resistance in BRCA2-mutated cancers; Nature; 2008; 451(7182):1116-1120.

Sang-Wook et al. "Genetic classification of colorectal cancer based on chromosomal loss and microsatellite instability predicts survival", Clinical Cancer Research, The American Association for Cancer Research, US, vol. 8, No. 7, Jul. 1, 2002 (Jul. 1, 2002), pp. 2311-2322, XP002593153, ISSN 1078-0432 *abstract*.

Silva et al., "Loss of heterozygosity in BRCA1 and BRCA2 markers and high-grade malignancy in breast cancer," Breast Cancer Res. & Treatment, Jan. 1999, vol. 53, No. 1, pp. 9-17.

Smid et al. "Patterns and incidence of chromosomal instability and their prognostic relevance in breast cancer subtypes", Breast Cancer Research and Treatment, Kluwer Academic Publishers, BO, vol. 128, No. 1, Jul. 15, 2010 (Jul. 15, 2010), pp. 23-30, XP019916000, ISSN: 1573-7217, DOI: 10.1007/S10549-010-1026-5, abstract; figures 1-3.

Stefansson et al; Genomic profiling of breast tumours in relation to BRCA abnormalities and phenotypes; Breast Cancer Res; 2009; 11(4):R47, 14 pages.

Tan et al.; 'BRCAness' syndrome in ovarian cancer: a case-control study describing the clinical features and outcome of patients with epithelial ovarian cancer asociated with BRCA1 and BRCA2 mutations; J Clin Oncol; 2008;26 (34):5530-5536.

The Cancer Genome Atlas Research Network; Integrated genomic analyses of ovarian carcinoma; Nature; 2011; 474(7353):609-615.

Vollenbergh et al. "Genomic instability in breast and ovarian cancers: translation into clinical predictive biomarkers", CMLS Cellular and Molecular Life Science, Birkhauser-Verlag, BA, vol. 69, No. 2, Sep. 16, 2011 (Sep. 16, 2011), pp. 223-245, XP019993251, ISSN: 1420-9071, DOI: 10.1007/S00018-011-0809-0, the whole document.

Wilcox et al.; High-resolution methylation analysis of the BRCA1 promoter in ovarian tumors; Cancer Genet Cytogenet; 2005; 159(2): 114-122.

Abkevich et al. "Patterns of genomic loss of heterozygosity predict homologous recombination repair defects in epithelial ovarian cancer", British Journal of Cancer, vol. 107, No. 10, Oct. 9, 2012 (Oct. 9, 2012), pp. 1776-1782, XP055085758, ISSN: 0007-0920, DOI: 10.1038/bjc.2012.451 *the whole document*.

Abkevich et al. "Supplemental Material: Table S1: Validation of copy number determinations by Real Time PCR SNP ID Adjacent Gene Sample Number By Real-Time PCR Number By CCNT SNP A",—1712744 CDKN2A HF505 0.010 0.47 HF1382 0.14 0, Oct. 1, 2006 (Oct. 1 2006), pp. 5-1713144, XP055085899, Retrieved from the Internet: URL: http://cancerres.aacrjournals.org/content/suppl/

(56) References Cited

OTHER PUBLICATIONS

2006/10/04/66.19.9428.DC2/ Supplementary_Tables_1-5.pdf [retrieved on Oct. 29, 2013] the whole document.
Al-Mulla et al., "Metastatic recurrence of early-stage colorectal cancer is linked to loss of heterozygosity on chromosomes 4 and 14q" Journal of Clinical Pathology, vol. 59, No. 6, pp. 624-630 (2006) See whole document.
Ashworth et al. "A Synthetic Lethal Therapeutic Approach: Poly(ADP) Ribose Polymerase Inhibiors for the Treatment of Cancers Deficient in DNA Double-Strand Break Repair", Journal of Clinical Oncology, vol. 26, No. 22, Aug. 1, 2008 (Aug. 1, 2008), pp. 3785-3790, XP055039560, ISSN: 0732-183X, DOI: 10.1200/JCO.2008.16/0812, abstract.
Beroukhim et al. "Inferring Loss-of-Heterozygosity from Unpaired Tumors Using High-Density Oligonucleotide SNP Arrays", Bioinformatics, vol. 19, No. 5, Jan. 1, 2006 (Jan. 1, 2006), p. 2397, XP055085786, ISSN: 1367-4803, DOI: 1367-4803 (2003)019[2397:AFLGM]2.0.CO; 2 *abstract* *p. 329, col. 1, paragraph 4—col. 2, line 1; table 2*.
Birkbak et al. "Telomeric allelic imbalance indicates defective DNA repair and sensitivity to DNA-damaging agents"; Cancer Discov; 2012; 2(4): 366-375; doi: 10.1158/2159-8290.CD-11-0206.
Bryant et al. "Specific killing of BRCA2-deficient tumours with inhibitors of poly(ADP-ribose) polmerase"; Nature; 2005; 434(7035):913-917.
Calvert et al. "245 Invited PARP inhibitors in cancer treatment", European Journal of Cancer. Supplement, Pergamon, Oxford, GB, vol. 6, No. 12, Oct. 1, 2008 (Oct. 1, 2008), p. 80, XP025534307, ISSN: 1359-6349 DOI: 10.1016/S1359-6349 (08) 72177-3 [retrieved on Oct. 1, 2008] abstract.
Cerbinskaite et al.; Defective homologous recombination in human cancers; Cancer Treat Rev; 2012; Epub 2011; 38(2): 89-100; doi:10.1016/j.ctrv.2011.04.015.
Chang et al., "Assessment of plasma DNA levels, allelic imbalance, and CA 125 as diagnostic tests for cancer", Journal of the National Cancer Institute, vol. 94, No. 22, pp. 1697-1703 (2002) See whole document.
Dann et al.; BRCA1/2 mutations and expression: response to platinum chemotherapy in patients with advanced stage epithelial ovarian cancer; Gynecol Oncol; 2012;125(3):677-682.
De Soto et al. "The inhibition and treatment of breast cancer with poly (ADP-ribose) polymerase (PARP-1) inhibitors", International Journal of Biological Sciences, Ivyspring International Publisher, AU, vol. 2, No. 4, Jun. 10, 2006 (Jun. 10, 2006), pp. 179-185, XP007906272, ISSN: 1449-2288, abstract.
Edwards et al.; Resistance to therapy caused by intragenic deletion in BRCA2; Nature; 2008; 451(7182):1111-1115.
Extended European Search Report, for application EP11796544.2, filed Nov. 18, 2013.
Farmer et al.; Targeting DNA repair defect in BRCA mutant cells as a therapeutic strategy; Nature; 2005; 434 (7035):917-921.
Filopanti et al., "Loss of heterozygosity at the SS receptor type 5 locus in human GH- and TSH—secreting pituitary adenomas," J. Endocrinol. Invest., Nov. 2004, vol. 27, No. 10, pp. 937-942.
Friedenson; BRCA1 and BRCA2 pathways and the risk of cancers other than breast or ovarian; MedGenMed; 2005; 7(2):60, 25 pages.
Gelmon et al.; Olaparib in patients with recurrent high-grade serous or poorly differentiated ovarian carcinoma or triple-negative breast cancer: a phase 2, multicentre, open-label, non-randomised study; Lancet Oncol; 2011;12 (9):852-861.
Goransson et al. "Quantification of Normal Cell Fraction and Copy Number Neutral LOH in Clinical Lung Cancer Samples Using SNP Array Data", PLOS ONE, vol. 4, No. 6, Jun. 26, 2009 (Jun. 26, 2009), p. e6057, XP055085703, ISSN: 1932-6203, DOI: 10.1371/journal.pone.0006057 *the whole document*.
Gorringe et al. "Are there any more ovarian tumor suppressor genes? A new perspective using ultra high-resoution copy number and loss of heterozygosity analysis", Genes Chromosomes & Cancer, John Wiley & Sons, Inc, US, vol. 48, No. 10, Oct. 1, 2009 (Oct. 1, 2009), pp. 931-842, XP002703162, ISSN: 1045-2257, DOI: 10.1002/GCC.20694 [retrieved on Jul. 14, 2009] *abstract* *p. 932, col. 2, paragraph 2-paragraph3*.
Graziani et al. "PARP-1 inhibition to treat cancer, ischemia, inflammation", Pharmacological Research, Academic Press, London, GB, vol. 52, No. 1, Jul. 1, 2005 (Jul. 1, 2005), pp. 1-4, XP004902631, ISSN: 1043-6618, DOI: 10.1016/J.PHRS.2005.02.007, the whole document.
Gudmundsdottir et al. "The roles of BRCA1 and BRCA2 and associated proteins in the maintenance of genomic stability", Oncogene, vol. 25, No. 43, Sep. 25, 2006 (Sep. 25, 2006), pp. 5864-5874, XP055040467, ISSN: 0950-9232, DOI: 10.1038/sj.onc.1209874, figure 1.
Gunnarsson et al. "Large but not small number alterations correlate to high-risk genomic aberrations and survival in chronic lymphocytic lukemia: a high-resolution genomic screening of newly diagnosed patients", Lukemia, vol. 24, No. 1, Jan. 1, 2010 (Jan. 1, 2010), pp. 211-215, XP055085701, ISSN: 0887-6924, DOI: 10.1038/leu.2009.187 *the whole document*.
Hampton et al., "Simultaneous assessment of loss of heterozygosity at multiple microsatellite loci using semi-automated fluorescence-based detection: Subregional mapping of chromosome 4 in cervical carcinoma," PNAS, Jun. 1996, vol. 93, No. 13, pp. 6704-6709.
Hennessy et al.; Somatic mutations in BRCA 1 and BRCA2 could expand the number of patients that benefit from poly (ADP ribose) polymerase inhibitors in ovarian cancer; J Clin Oncol; 2010; 28(22):3570-3576.
Holstege et al.; BRCA1-mutated and basal-like breast cancers have similar aCGH profiles and a high incidence of protein truncating TP53 mutations; BMC Cancer; 2010; 10:654, 15 pages.
International Search Report, for application PCT/EP2013/061707, mailed on Jul. 29, 2013.
International Search Report, for application PCT/US2011/040953, mailed on Feb. 27, 2012.
International Search Report, for application PCT/US2011/048427, mailed on Nov. 7, 2011.
International Search Report, for application PCT/US2012/042668, mailed on Feb. 1, 2013.
International Search Report, for application PCT/US2012/071380, mailed on Apr. 12, 2013.
International Search Report, for application PCT/US2013/027295, mailed on Jun. 10, 2013.
Janne et al. "High-resolution single-nucleotide polymorphism array and clustering analysis of loss of heterozygosity in human lung cancer cell lines", Oncogene, vol. 23, No. 15, Mar. 29, 2004 (Mar. 29, 2004), pp. 2716-2726, XP055085726, ISSN: 0950-9232, DOI: 10.1038/sj.onc.1207329 *abstract*.
Joosse et al. "Prediction of BRCA-1—association in hereditary non-BRCA1/2 breast carcinomas with array-CGH", Breast Cancer Research and Treatment, Kluwer Academic Publishers, BO, vol. 116, No. 3, Aug. 14, 2008 (Aug. 14, 2008), pp. 479-489, XP019727887, ISSN: 1573-7217, abstract.
Ko et al., "Frequent loss of heterozygosity on multiple chromosomes in Chinese esophageal squamous cell carcinomas" Cancer Letters, vol. 170, No. 2, pp. 131-138 (2001) See whole document.
Kujawski et al. "Genomic complexity identifies patients with agressive chronic lymphocytic lukemia", Blood, vol. 112, No. 5, Sep. 1, 2008 (Sep. 1, 2008), pp. 1993-2003, XP055085975, iSSN: 0006-4971, DOI: 10.1182/blood-2007-07-099432 *the whole document*.
Lemeta et al., "Loss of Heterozygosity at 6q is Frequent and Concurrent with 3p Loss in Sporadic and Familial Capillary Hemangioblastomas," J. Neuropathol. Exp. Neurol., Oct. 2004, vol. 63, No. 10, pp. 1072-1079.
Leunen et al. "Recurrent Copy number alterations in BRCA1—mutated ovarian tumors alter biological pathways", Human Mutation, vol. 30, n. 12, Dec. 1, 2009 (Dec. 1, 2009), pp. 1693-1702, XP055040581, ISSN: 1059-7794, DOI: 10.1002/humu.21135 *abstract* *paragraph bridging p. 1694-1965; figures 2B, 3, 4*.
Loveday et al.; Germline mutations in RAD51D confer susceptibility to ovarian cancer; Nat Genet; 2011; 43 (9):879-882.
Marsit et al.; Inactivation of the Fanconi anemia/BRCA pathway in lung and oral cancers: implications for treatment and survival; Oncogene; 2004; 23(4):1000-1004.

(56) References Cited

OTHER PUBLICATIONS

Matsumoto et al., "Allelic imbalance at 1P36 may predict prognosis of chemoradiation therapy for bladder preservation in patients with invasive bladder cancer", British Journal of Cancer, vol. 91, No. 6, pp. 1025-1031 (2004), See abstract: pp. 1027, 1030; and tables 3-4.
Meadows et al. "Genome-wide analysis of loss of heterozygosity and copy number amplification in uterine leiomyomas using the 100k single nucleotide polymorphism array", Experimental and Molecular Pathology, vol. 91, No. 1, Apr. 8, 2011 (Apr. 8, 2011), pp. 434-439, XP028239924, ISSN: 0014-4800, DOI: 10.1016/J.YEXMP.2011.03007 [retrieved on Apr. 8, 2011] *abstract, conclutions; p. 438 col. 2 par. 3*.
Meindl et al.; Germline mutations in breast and ovarian cnacer pedigrees establish RAD51C as a human cancer susceptibility gene; Nat Genet; 2010; 42(5):410-414.
Mendes-Pereira et al.; Synthetic lethal targeting of PTEN mutant cells with PARP inhibitors; EMBO Mol Med; 2009;1(6-7): 315-322.
Nannya et al. "A Rubust Algorithm for Number Detection Using High-Density Oligonucleotide Single Nucleotide Polymorphism Genotyping Arrays", Cancer Research, American Association for Cancer Research, US, vol. 65, No. 14, Jul. 14, 2005 (Jul. 14, 2005), pp. 6071-6079, XP008155967, ISSN: 0008-5472, DO1:10.1158/0008-5472.CAN-05-0465 Retrieved from the internet: URL: http://cancerres.aacrjournals.org [retrieved on Jul. 15, 2005] *the whole document*.
Narayan et al.; Frequent promoter of methylation of CDH1,DAPK,RARB, and HIC1 genes in carcinoma of cervix uteri: its relationship to clinical outcome; Mol Cancer; 2003;2:24, 12 pages.
Norquist et al.; Secondary somatic mutations restoring BRCA1/2 predict chemotherapy resistance in herditary ovarian carcinomas; J Clin Oncol;2011; 29(22): 3008-3015.
Osborne et al., "A genome-wide map showing common regions of loss of heterozygosity/allelic imbalance in breast cancer", Cancer Research, vol. 60, No. 14, pp. 3706-3712 (2000) See whole document.
O'Shaugnessy et al.; Iniparib plus chemotherapy in metastatic triple-negative breast cancer; N. Engl J Med; 2011; 364(3):205-214.
Penning et al., "Discovery and SAR of 2-(1-propylpiperidin-4-yl)-1H-benzimidazole-4-carboxamide: A potent inhibitor of poly(ADP-ribose) polymerase (PARP) for the treatment of cancer", Bioorganic & Medicinal Chemistry, Pergamon, GB, vol. 16, No. 14, Jul. 15, 2008 (Jul. 15, 2008), pp. 6965-6975, XP022941564, ISSN: 0968-0896, DOI 10.1016/J.BMC.2008.05.044 [retrieved on May 27, 2008] abstract.
Birbak et al., Cancer Research, 72(8):1, (2012). Abstract 4823: copy number gain and increased expression of BLM and FANCI is associated with sensitivity to genotoxic chemotherapy in triple negative breast and serious ovarian cancer.
Arlt et al., Molecular and Cellular Biology, 24(5):6701-6709 (2004). "BRCA1 is required for common-fragile-site stability via its G2M checkpoint function."
Bamford et al., British Journal of Cancer 91:355-358 (2004). "The COSMIC (Catalogue of Somatic Mutations in Cancer) database and website."
Bell et al., Nature 474:609-615 (2011). "Intergrated genomic analyses of ovarian carcinoma."
Bengtsson et al., Bioinformatics 25(17):2149-2156 (2009). "A single-array preprocessing methos for estimating full-resolution raw copy numbers from all affymetrix genotyping arrays includig genomeWideSNP 5 & 6."
Bengtsson et al., BMC Bioinformatics 11:245-262 (2010). "TumorBoost: Normalization of allele-specific tumor copy numbers from a singe pair of tumor-normal genotyping microarrays."
Bouwman et al., Nature Structural and Molecular Biology 17(6):688-696 (2010). "53BP1 loss rescues BRCA1 deficiency and is associated with triple-negative and BRCA-mutated breast cancers."
Byrski et al., Breast Cancer Res Treat. 115(2):359-63. (2009). Response to neoadjuvant therapy with cisplatin in BRCA1-positive breast cancer patients.
Bunting et al., Cell. 141(2):243-54 (2010). "53BP1 inhibits homologous recombination in Brca1-deficient cells by blocking resection of DNA breaks."
Burger et al. Drug Resistance Updates 14:22-34 (2011). 'Drug transporters of platinum-based anticancer agents and their clinical significance.'
Cass et al., Cancer. 97(9):2187-95 (2003). "Improved survival in women with BRCA—associated ovarian carcinoma.".
Cha et al., Science. ;297(5581):602-6 (2002). "ATR homolog Mec1 promotes fork progression, thus averting breaks in replication slow zones."
Hasting et al., PLOS Genetics 5(1):e1000327 (2009). "A microhomology-mediated break-induced replication model for the origin of human copy number variation."
Hastings et al., Nat Rev. Genetic 10(8):551-564 (2009). "Mechanisms of change in gene copy number."
Heiser et al., Proc Natl Acad Sci U S A. 109(8):2724-9 (2012). "Subtype and pathway specific responses to anticancer compounds in breast cancer."
Iafrate et al., Nat Genet. 36(9):949-51. (2004). "Detection of large-scale variation in the human genome."
Kalb et al., Genome Dyn. 1:218-42. (2006). "Fanconi anemia: causes and consequences of genetic instability."
Kolomietz et al., Genes Chromosomes Cancer. 35(2):97-112 (2002). "The role of Alu repeat clusters as mediators of recurrent chromosomal aberrations in tumors."
Lakhani et al., Clin Cancer Res. 11(14):5175-80 (2005). "Prediction of BRCA1 status in patients with breast cancer using estrogen receptor and basal phenotype."
Li et al.,Nature Medicine 16(2):214-219 (2010). Amplication of LAPTM4B and YWHAZ contributes to chemotherapy resistance and recurrence of breast cancer.
Li et al., BMC Bioinformatics 12:474 (2011). "Jetset: selecting the optimal microarray probe set to represent a gene."
Luo et al., Nat Genet. 26(4):424-9 (2000). "Cancer predisposition caused by elevated mitotic recombination in Bloom mice."
McVean et al., Philos Trans R Soc Lond B Biol Sci. 365(1544):1213-8 (2010). "What drives recombination hotspots to repeat DNA in humans?".
Ogston et al., Breast. 2(5):320-7 (2003). "A new histological grading system to assess response of breast cancers to primary chemotherapy: prognostic significance and survival."
Puliti et al., Mutat Res. 686(1-2):74-83 (2010). "Low-copy repeats on chromosome 22q11.2 show replication timing switches, DNA flexibility peaks and stress inducible asynchrony, sharing instability features with fragile sites."
Richard et al., Microbiol Mol Biol Rev. 72(4):686-727 (2008). "Comparative genomics and molecular dynamics of DNA repeats in eukaryotes."
Richardson et al., Cancer Cell 9:121-132 (2006). "X chromosomal abnormalities in basal-like human breast cancer".
Ryan et al., 2009 ASCO Annual Meeting, http://meetinglibrary.asco.org/content/34135-65, (2009). Neoadjuvant cisplatin and bevacizumab in triple negative breast cancer (TNBC): Safety and efficacy.
Samouelian et al., Cancer Chemother Pharmacol. 54(6):497-504 (2004). "Chemosensitivity and radiosensitivity profiles of four new human epithelial ovarian cancer cell lines exhibiting genetic alterations in BRCA2, TGFbeta-RII, KRAS2, TP53 and/or CDNK2A."
Schwartz et al., Genes Development 19:2715-2726 (2005). "Homologous recombination and nonhomologous end-joining ning repair pathways regulate fragile site stability."
Sebat et al., Science. 305(5683):525-8 (2004). "Large-scale number polymorphism in the human genome."
Silver et al., Cell 128(5):991-1002 (2007). "Further evidence for BRCA1 communication with the inactive X chromosome."
Sorlie et al., PNAS 100(14):8418-8423 (2003). "Repeated observation of breast tumor subtypes in independent gene expression data set."

(56) References Cited

OTHER PUBLICATIONS

Stankiewicz et al., Am J Hum Genet. 72(5):1101-16 (2003). "Genome architecture catalyzes nonrecurrent chromosomal rearrangements."
Swisher et al. Cancer Res. 68(8):2581-6 (2008). "Secondary BRCA1 mutations in BRCA1—mutated ovarian carcinomas with platinum resistance."
Tassone et al., Br J Cancer. 88(8):1285-91 (2003). "BRCA1 expression modulates chemosensitivity of BRCA1—defective HCC1937 human breast cancer cells."
Turner et al., Oncogene 26:2126-2132 (2007). "BRCA1 dysfuntion in sporadic basal-like breast cancer."
Van Loo et al.,PNAS 107(39):16910-16915 (2010). "Allele-specific copy number analysis of tumors."
Vrieling et al., Nature Genetics 28:101-102 (2001). "Mitotic maneuvers in the light."
Wang et al., Cancer Research 64:64-71 (2004). "Loss of heterozygosity and it's correlation with expression profiles in subclasses of invasive breast cancers."
Wang et al., Genome Biology 8:R246 (2007). "Analysis of molecular inversion probe performance for allele copy number determination"
Xu et al., Molecular Cell 3:389-395 (1999). "Centrosome amplification and a defective G2-M cell cycle checkpoint induce genetic instability in BRCA1 Exon 11 Isoform-deficient cells."
Yang et al. Cancer Research 61:348-354 (2001). "Reconstitution of caspase 3 sensitizes MCF-7 Breast Cancer to Doxoubicin- and Etoposide-induced apoptsis."
Argos et al. "Genomewide scan for loss of heterozygosity and chromosomal amplification in breast carcinoma using single-nucleotide polymorphism arrays", Cancer Genetics and Cytogenetics, vol. 182, No. 2, Apr. 15, 2008.
European Search Report, from Application EP12801070.9, completed on Nov. 21, 2014.
European Search Report, from Application EP12860530.0, completed on Jul. 7, 2015.
Fang et al. "Genomic Differences Between Estrogen Receptor (ER)-Positive and ER-Negative Human Breast Carcinoma Identified by Single Nucleotide Polymorphism Array Comparative Genome Hybridization Analysis", Cancer, vol. 117, No. 10, May 2011.
Hendricks et al. "'Recombomice': The past, present, and future of recombination-detection in mice" DNA Repair, vol. 3, No. 10, Oct. 5, 2004.1.
International Search Report, for application PCT/EP2014/076786, filed Dec. 5, 2014.
International Search Report, for application PCT/US2011/026098, filed Feb. 24, 2011.
Isakoff et al., "TBCRC009: A Multicenter Phase II Clinical Trial of Platinum Monotherapy With Biomarker Assessment in Metastatic Triple-Negative Breast Cancer," J Clin Oncol, 2015, 1-8.
Kaklamani et al., "Phase II neoadjuvant clinical trial of carboplatin and eribulin in women with triple negative early-stage breast cancer (NCT01372579)," Breast Cancer Res Treat, 2015, 151:629-638.
Lin et al. "Integrated analysis of number alterations and loss of heterozygosity in human pancreatic cancer using a high-resolution, single nucleotide polymorphism array", Oncology, vol. 75, No. 1-2, Sep. 1, 2008.
Maeck et al. "Genetics instability in myelodysplastic syndrome: Detection of microsatellite instability and loss of heterozygosity in bone marrow samples with karyotype alterations" British Journal of Haematology, vol. 109, No. 4, Jun. 2000.
Mateo et al., "Appraising iniparib, the PARP inhibitor that never was—what must we learn?," Nature, Dec. 2013, 10: 688-696.
Mei et al.: "Genome-wide detection of Allelic Imbalance Using Human SNPs and High-density DNA arrays", Genome Research, vol. 10, No. 8, Aug. 1, 2000, pp. 1126-1137.
Mukhopadhyay et al., "Clinicopathological Features of Homologous Recombination-Deficient Epithelial Ovarian Cancers: Sensitivity to PARP Inhibitors, Platinum, and Survival," Cancer Research, 72(22), 2012, 5675-5682.
Novak et al: "A high-resolution allelotype of B-cell chronic lymphocytic leukemia (B-CLL)", Blood, American Society of Hematology, US, vol. 100, No. 5, Sep. 1, 2002, pp. 1787-1794.
Patel et al., "Failure of Iniparib to Inhibit Poly(ADP-Ribose) Polymerase In Vitro," Clin Cancer Res, 2012, 1655-1662.
Peng et al., "Genome-wide transcriptome profiling of homologous recombination DNA repair," Nature Communications, 2014, 1-11.
Schouten et al., "Challengers in the Use of DNA Repair Deficiency as a Biomarker in Breast Cancer," Journal of Clinical Oncology, 2015, 33(17): 1867-1869.
Telli et al., "Phase II Study of Gemcitabine, Carboplatin, and Iniparib as Neoadjuvant Therapy for Triple-Negative and BRCA1/2 Mutation-Associated Breast Cancer With Assessment of a Tumor-Based Measure of Genomic Instability: PrECOG0105," J Clin Oncol, 2015, 1-7.
Volchenboum et al. "Comparison of Primary Neuroblastoma Tumors and Derivative Early-Passage Cell Lines Using Genome-Wide Single Nucleotide Polymorphism Array Analysis", Cancer Research, vol. 69, No. 10, May 15, 2009.
Wilcoxen et al., "Homologous recombination deficiency (HRD) score enriches for niraparib sensitive high grade ovarian tumors," Supplemental Abstract, 2015, 1 page.
Wilcoxen et al., "Use of homologous recombination deficiency (HRD) score to enrich for niraparib sensitive high grade ovarian tumors, "J Clin Oncol, 2015, Supplemental Abstract: 5532, 2 pages.
Xiao et al., "The XIST Noncoding RNA Functions Independently of BRCA1 in X Inactivation," Cell, Mar. 2007, 128:977-989.
Juul et al., Cancer Research, 69(24):509S-510S (2009). "A Genomic-Profile Derived Summary Measure of Chromosomal Breakpoints Predicts Response to Treatment with the DNA-Damaging Agent Cisplatin."
Ott et al., Clinical Cancer Research, The American Association for Cancer Research, US, 9(6):2307-2315 (2003). "Chromosomal Instability rather than p53 mutation is associated with response to neoadjuvant cisplatin-based chemotherapy in gastric carcinoma".
Takahashi, Clinical Cancer Research, 13(1):111-120 (2007). "Clonal and Parallel Evolution of Primary Lung Cancers and Their Metastases Revealed by Molecular Dissection of Cancer Cells."
Ferreira et al, "Array CGH and gene-expression profiling reveals distinct genomic instability patterns associated with DNA repair and cell-cycle checkpoint pathways in Ewing's sarcoma", Oncogene, vol. 27, No. 14, pp. 2084-2090, 2008.
Etemadmoghadam et al, "Integrated genome-wide DNA copy number and expression analysis identifies distinct mechanism of primary chemoresistance in ovarian carcinomas", Clinical Cancer Research, The American Association for Cancer Research, vol. 15, No. 4, pp. 1417-1427, 2009.
Silver et al, "Efficacy of Neoadjuvant Cisplatin in Triple-Negative Breast Cancer", Journal of Clinical Oncology, vol. 28, No. 7, pp. 1145-1153, 2010.
European Communication Response for application 11757992.0, dated Mar. 21, 2014.
European Communication Response for application 11757992.0, dated Dec. 9, 2014.
European Communication Response for application 11796544.2, dated Sep. 28, 2015.
European Communication Response, for application 11796544.2, dated Feb. 1, 2016.
European Communication Response, for application 11796544.2, dated Aug. 3, 2015.
European Communication Response, for application 12860530.0, dated Feb. 10, 2016.
European Communication, for application 11757992.0, dated Aug. 5, 2014.
European Communication, for application 11757992.0, dated Dec. 10, 2013.
European Communication, for application 11796544.2, dated Jan. 20, 2016.
European Communication, for application 11796544.2, dated May 11, 2015.

(56) References Cited

OTHER PUBLICATIONS

European Communication, for application 11796544.2, dated Sep. 11, 2015.
European Communication, for application 12801070.9, dated Apr. 1, 2016.
European Intention to Grant, for application 11757992.0, dated Jul. 28, 2015.
European Intention to Grant, for application 11796544.2, dated Mar. 31, 2016.
Extended European Search Report, for application EP15189527.3, dated Mar. 31, 2016.
Fontanillas et al., "Key considerations for measuring allelic expression on a genomic scale using high-throughput sequencing", Molecular Ecology, 19(1): 212-227 (2010).
Heap et al., "Genome-wide analysis of allelic expression imbalance in human primary cells by high-throughput transcriptome resequencing", Human Molecular Genetics, 19(1):122-134 (2010).
International Preliminary Report on Patentability, app. No. PCT/US2012/071380, dated Jun. 24, 2014.
International Search Report, for application PCT/US2015/045561, dated Nov. 9, 2015.
Japanese Patent Application Kohyo Publication No. (JP-A) 2008-538496 (unexamined Japanese national phase publication corresponding to a non-Japanese international publication).
Johansson et al., "Abstract 4833: A genomic portrait of tumor progression using next-generation sequencing", Cancer Res., 71: 4833 (2011).
Patocs et al., "Breast-cancer stromal cells with TP53 mutations and nodal metastases", N. Engl. J. Med., 357:2543-2551 (2007).
Popova et al., "Ploidy and Large-Scale Genomic Instability Consistently Identify Basal-like Breast Carcinomas with BRCA1/2 Inactivation", Cancer Research, 72(21); 5454-62 (2012).
Santana-Davila et al., "Treatment options for patients with triple-negative breast cancer", Journal of Hematology & Oncology, 3:42 (2010).
Tai et al., "High-Throughput Loss-of-Heterozygosity Study of Chromosome 3p in Lung Cancer Using Single-Nucleotide Polymorphism Markers", Cancer Research, 66(8): 4133-4138 (2006).
Tuna et al., "Association between Acquired Uniparental Disomy and Homozygous Mutations and HER2/ER/PR Status in Breast Cancer", PLoS One 5(11):e15094 (2010).
Walsh et al., "Genome-Wide Loss of Heterozygosity and Uniparental Disomy in BRCA1/2-Associated Ovarian Carcinomas", Clin Cancer Res., 14(23): 7645-7651 (2008).
Zhao et al., "Systematic detection of putative tumor suppressor genes through the combined use of exome and transcriptome sequencing", Genome Biol., 11: R114,1-14 (2010).

* cited by examiner

A

B

METHODS FOR PREDICTING ANTI-CANCER RESPONSE

CROSS-REFERENCE TO RELATED APPLICATIONS

This application is a 35 U.S.C. §371 National Phase Entry Application of International Application No. PCT/US2011/048427, filed Aug. 19, 2011, which designates the United States, and which claims the benefit under 35 U.S.C. 119(e) of U.S. Provisional Application No. 61/402,116 filed on Aug. 24, 2010, the contents of which are herein incorporated into this application bt reference in their entirety.

GOVERNMENT FUNDING

This invention was made with government support under Grant No. CA089393097193 awarded by The National Institutes of Health. The government has certain rights in the invention.

BACKGROUND OF THE INVENTION

Medical oncologists have benefited greatly from relatively recent efforts to dissect and understand the genetic elements underlying mammalian cancer. The identification of specific genetic predispositions, such as mutations in BRCA-1, BRCA2, and HER2, has provided key insights into the mechanisms underlying tumorigenesis and has proven useful for the design of new generations of targeted approaches for clinical intervention. With the determination of the human genome sequence and improvements in sequencing and bioinformatics technologies, systematic analyses of genetic alterations in human cancers have become possible. However, clinical interventions based upon this information have been severely hampered by the fact that often only a percentage of patients will respond favorably to a particular anti-cancer treatment. Medical oncologists currently cannot generally predict which patients will or will not respond to a proposed chemotherapeutic treatment. Accordingly, there is a great need in the art to identify patient responsiveness to particular anti-cancer therapies.

SUMMARY OF THE INVENTION

The present invention is based, at least in part, on the discovery that certain patterns of DNA aberrations described herein are predictive of anti-cancer response of the cells harboring such DNA aberrations to anti-cancer therapies. Accordingly, in one aspect, the present invention features a method for predicting the outcome of anti-cancer treatment of a subject with a cell hyperproliferative disorder, comprising determining a global chromosomal aberration score (GCAS), comprising obtaining a biological sample from the subject and determining whether a plurality of chromosomal regions displaying a chromosomal aberration exists within a plurality of chromosomal loci, wherein said chromosomal aberrations are selected from the group consisting of allelic imbalance (AI), loss of heterozygosity (LOH), copy number aberrations (CNA), copy number gain (CNG), copy number decrease (CND) and combinations thereof, relative to a control, and wherein the presence of a plurality of chromosomal regions displaying said chromosomal aberrations predicts the outcome of anti-cancer treatment of the subject. The subject can be a mammal, such as a human.

In one aspect, the anti-cancer treatment is chemotherapy treatment. In another embodiment, the anti-cancer treatment comprises platinum-based chemotherapeutic agents (e.g., cisplatin, carboplatin, oxaliplatin, nedaplatin, and ipropla-tin).

In another aspect, the cell hyperproliferative disorder is selected from the group consisting of breast cancer, ovarian cancer, transitional cell bladder cancer, bronchogenic lung cancer, thyroid cancer, pancreatic cancer, prostate cancer, uterine cancer, testicular cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, Kaposi's sarcoma, Ewing's tumor, refractory multiple myeloma, and squamous cell carcinomas of the head, neck, cervix, and vagina.

In still another aspect, the biological sample is selected from the group consisting of cells, cell lines, histological slides, frozen core biopsies, paraffin embedded tissues, formalin fixed tissues, biopsies, whole blood, nipple aspirate, serum, plasma, buccal scrape, saliva, cerebrospinal fluid, urine, stool, and bone marrow. In one embodiment, the biological sample is enriched for the presence of hyperproliferative cells to at least 75% of the total population of cells. In another embodiment, the enrichment is performed according to at least one technique selected from the group consisting of needle microdissection, laser microdissection, fluorescence activated cell sorting, and immunological cell sorting. In still another embodiment, an automated machine performs the at least one technique to thereby transform the biological sample into a purified form enriched for the presence of hyperproliferative cells. IN yet another embodiment, the biological sample is obtained before the subject has received adjuvant chemotherapy. Alternatively, the biological sample is obtained after the subject has received adjuvant chemotherapy.

In yet another aspect, the control is determined from a non-cell hyperproliferative cell sample from the patient or member of the same species to which the patient belongs. In one embodiment, the control is determined from the average frequency of genomic locus appearance of chromosomal regions of the same ethnic group within the species to which the patient belongs. In another embodiment, the control is from non-cancerous tissue that is the same tissue type as said cancerous tissue of the subject. In still another embodiment, the control is from non-cancerous tissue that is not the same tissue type as said cancerous tissue of the subject.

In another aspect, AI is determined using major copy proportion (MCP). In one embodiment, AI for a given genomic region is counted when MCP is greater than 0.70.

In still another aspect, the plurality of chromosomal loci are randomly distributed throughout the genome at least every 100 Kb of DNA. In one embodiment, the plurality of chromosomal loci comprise at least one chromosomal locus on each of the 23 human chromosome pairs. In another embodiment, the plurality of chromosomal loci comprise at least one chromosomal locus on each arm of each of the 23 human chromosome pairs. In still another embodiment, the plurality of chromosomal loci comprise at least one chromosomal locus on at least one telomere of each of the 23 human chromosome pairs. In yet another embodiment, the plurality of chromosomal loci comprise at least one chromosomal locus on each telomere of each of the 23 human chromosome pairs.

In yet another aspect, the chromosomal aberrations have a minimum segment size of at least 1 Mb. In one embodiment, the chromosomal aberrations have a minimum segment size of at least 12 Mb.

In another aspect, the plurality of chromosomal aberrations comprises at least 5 chromosomal aberrations. In one embodiment, the plurality of chromosomal aberrations comprises at least 13 chromosomal aberrations.

In still another aspect, the chromosomal loci are selected from the group consisting of single nucleotide polymorphisms (SNPs), restriction fragment length polymorphisms (RFLPs), and simple tandem repeats (STRs).

In yet another aspect, the chromosomal loci are analyzed using at least one technique selected from the group consisting of molecular inversion probe (MIP), single nucleotide polymorphism (SNP) array, in situ hybridization, Southern blotting, array comparative genomic hybridization (aCGH), and next-generation sequencing.

In another aspect, the outcome of treatment is measured by at least one criteria selected from the group consisting of survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria.

In still another aspect, the method further comprises determining a suitable treatment regimen for the subject. In one embodiment, the suitable treatment regimen comprises at least one platinum-based chemotherapeutic agent when a plurality of genomic chromosomal aberrations is determined or does not comprise at least one platinum-based chemotherapeutic agent when no plurality of genomic chromosomal aberrations is determined.

BRIEF DESCRIPTION OF THE DRAWINGS

FIG. 1A shows a dose response curves of six TNBC cell lines as determined by a proliferation assay after 48 hours of cisplatin exposure. Curves for cells with lower $IC_{50}$ values (greater sensitivity) are shown in blue; the cell line with highest $IC_{50}$ (greatest resistance) is shown in red; cell lines with intermediate sensitivity are shown in grey. FIG. 1B shows the effect of the AI segment size threshold on the correlation between the number of telomeric AI regions and the cisplatin sensitivity in the six cell lines. Each point represent an $R^2$ value based on linear regression between the count of CNA regions of a minimum size indicated at X-axis, and cisplatin $IC_{50}$ in a panel of 6 TNBC cell lines (BT20, BT-549, HCC1187, HCC38, MDA-MB-231, MDA-MB-468). The optimum minimum segment size threshold is indicated by the dotted line. FIG. 1C shows a comparison between the number of telomeric AI regions ($N_{tAI,12}$) and cisplatin sensitivity at the selected optimum threshold of 12 Mb. The cell lines are indicated as follows: 1, BT-20; 2, BT-549; 3, HCC1187; 4, HCC38; 5, MDA-MB-231; 6, MDA-MB-468.

FIG. 2A shows the formula for calculation of MCP, as well as normal bi-allelic chromosomes and three different ways in which allelic imbalance of a chromosomal region may occur and the corresponding MCP calculation. FIGS. 2B and 2C show diagrams depicting the display of loss of heterozygosity (LOH), AI determined by MCP, and absolute copy number analysis in two tumor samples with different degrees of normal cell contamination: T7 with >95% tumor cell content (FIG. 2B) and T5 with approximately 80% tumor content (FIG. 2C). The chromosomes are indicated along the left side. The first columns for each tumor show the cells for LOH (blue) and retention of heterozygosity (yellow) at each chromosome position. The second columns show the MCP levels (between 0.5 and 1.0) at each chromosomal position. The MCP cut off of 0.7 is indicated by red lines. AI is called for regions with MCP greater than 0.7. The third and forth columns display the absolute DNA copy number at each position with white indicating diploid, shades of red indicating copy gain and shades of blue indicating copy loss. The copy number levels are shown in the far right panels. The tumor sample with greater purity (T7 in FIG. 2B), shows agreement between LOH and MCP-determined AI calls. In the tumor sample with only 80% tumor cells, the LOH signal is lost, but AI can still be estimated by MCP with a 0.70 threshold.

FIG. 3A shows cisplatin $IC_{50}$ versus number of telomeric AI regions at least 1 Mb long with AI defined by MCP>0.7. FIG. 3B shows cisplatin $IC_{50}$ versus count of regions with copy number aberration, including gains and losses, at least 1 Mb long. FIG. 3C shows cisplatin $IC_{50}$ versus count of regions with copy number gain, at least 1 Mb long. FIG. 3D shows cisplatin $IC_{50}$ versus count of regions with copy number loss, at least 1 Mb long. The cell lines are indicated on each figure and are the same as in FIG. 1.

FIG. 4A shows cisplatin $IC_{50}$ versus number of telomeric AI regions at least 1 Mb long with AI defined by MCP>0.7. FIG. 4B shows cisplatin $IC_{50}$ versus number of interstitial AI regions at least 1 Mb long with AI defined by MCP>0.7. The cell lines are indicated on each figure and are the same as in FIG. 1.

FIGS. 5A-5C show the determination of the minimum segment size that demonstrates the best correlation to cisplatin sensitivity for number of copy number aberrations (NCNA; FIG. 5A), number of regions with copy number gain (NCNA, gain; FIG. 5B), and number of regions with copy number loss (NCNA, loss; FIG. 5C). Each point represent an $R^2$ value based on linear regression between the count of CNA regions of a minimum size indicated at X-axis, and cisplatin $IC_{50}$ in a panel of 6 TNBC cell lines (BT20, BT-549, HCC1187, HCC38, MDA-MB-231, MDA-MB-468). The optimal minimum size of CNA regions is indicated by the dotted line. FIG. 5D-5F show plots of the cisplatin $IC_{50}$ values (µM, X-axis) vs. the number of CNA regions with optimum minimum segment sizes (Y-axis) as follows: NCNA at least 9 Mb long (FIG. 5D), NCNA, gain at least 9 Mb long (FIG. 5E), and NCNA, loss at least 5 Mb long, in 6 TNBC cell lines (FIG. 5F), as indicated.

FIG. 6A shows representations of individual tumor genomes arranged in order of increasing MP score. Regions of telomeric AI (dark blue) and interstitial AI (light blue) are indicated, with thin white lines demarcating individual chromosomes. FIG. 6B shows association between the MP score and the $N_{tAI,12}$. FIG. 6C shows a receiver operating characteristics (ROC) curve evaluating the performance of $N_{tAI,12}$ to predict pCR to cisplatin therapy (pCR, n=4; no pCR, n=20).

FIG. 8A shows a rank of individuals according to increasing $N_{tAI,12}$. Those who relapsed within one year are indicated by closed circles and those without relapse within one year are indicated by open circles. A cutoff value of $N_{tAI,12}$=13, based on the TNBC ROC analysis for prediction of pathologic complete response (pCR) to cisplatin, is indicated by the dotted line. FIG. 8B shows Kaplan-Meier survival curves for time to relapse in individuals classified as high $N_{tAI,12}$ (13 or greater $N_{tAI,12}$ regions, blue) or low $N_{tAI,12}$ (fewer than 13 $N_{tAI,12}$ regions, red).

DETAILED DESCRIPTION OF THE INVENTION

Figure 1:
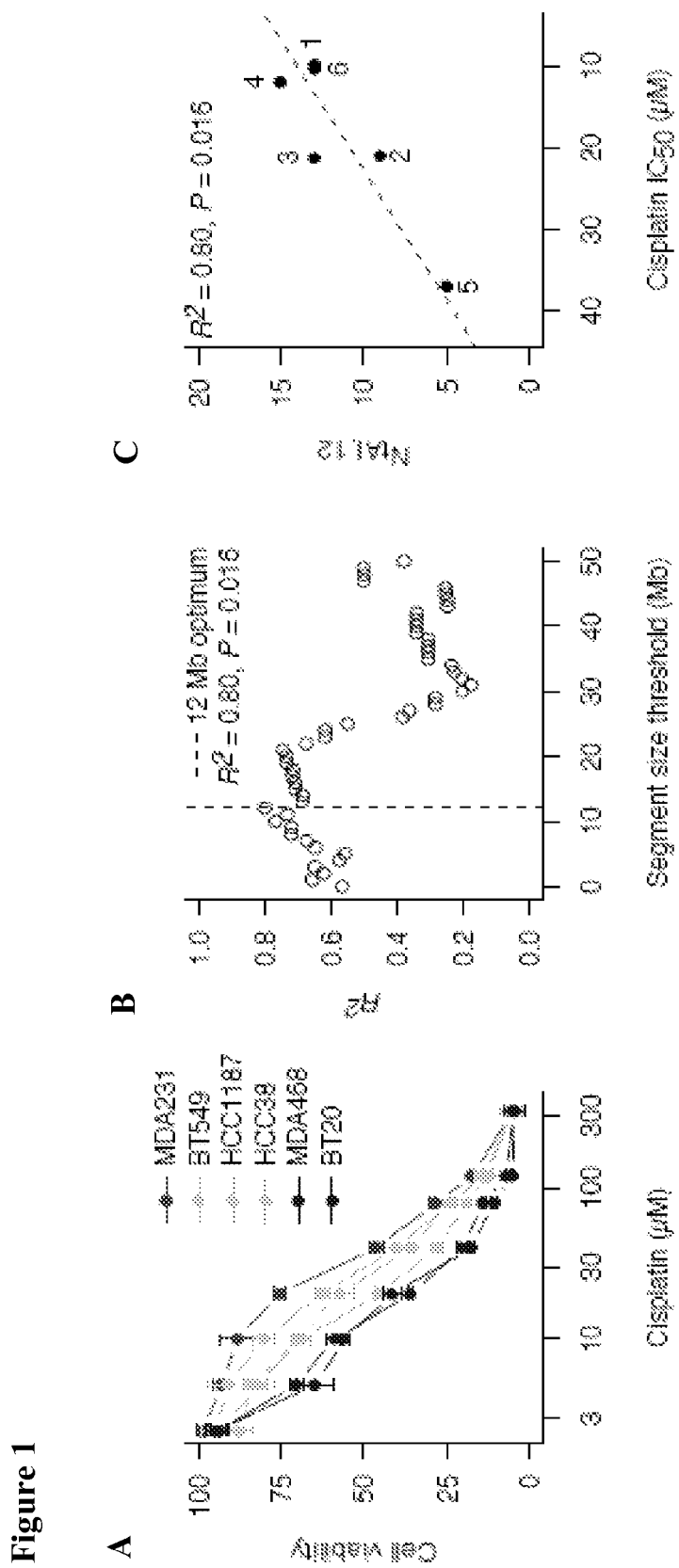
FIGS. 1A-1C show the correlation between allelic imbalance (AI) regions and cisplatin sensitivity in vitro.

The present invention relates to methods for predicting response of a cancer in a subject to anti-cancer therapies based upon a determination and analysis of a global chromosomal aberration score (GCAS).

I. Determining Global Chromosomal Aberration Score (GCAS)

According to one aspect of the invention, GCAS is a measurement predictive of responsiveness to anti-cancer therapies of a cancer in a subject. This utility of GCAS is based upon the novel finding that the summation of individual chromosomal aberrations can predict responsiveness of a cancer in a subject to anti-cancer agents independently of identifying specific chromosomal aberrations. Informative loci of interest (e.g., single nucleotide polymorphisms (SNPs), restriction fragment length polymorphisms (RFLPs), simple tandem repeats (STRs), etc.), are used to determine GCAS as they are useful for detecting and/or distinguishing chromosomal aberrations (e.g., allelic imbalance, loss of heterozygosity, total copy number change, copy number gain, and copy number loss).

GCAS is determined by determining a plurality or the total number of chromosome regions displaying allelic imbalance ($N_{AI}$), loss of heterozygosity (LOH), copy number aberrations ($N_{CNA}$), copy number gain ($N_{CNG}$), and/or copy number decrease ($N_{CND}$), as described further herein and according to methods well-known in the art. A GCAS of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 or more is predictive of response to anti-cancer therapy of the cancer cell from which the assayed nucleic acid was derived.

In one embodiment, the analysis is based upon nucleic acids obtained from a subject and/or control sample. Such samples can include "body fluids," which refer to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow.

In one embodiment, SNPs are used in determining GCAS, for predicting responsiveness of a cancer to an anti-cancer therapy. There are six possible SNP types, either transitions (A< >T or G< >C) or transversions (A< >G, A< >C, G< >T or C< >T). SNPs are advantageous in that large numbers can be identified.

In some embodiments, the SNPs or other genomic loci can be scored to detect copy number abnormalities. In such cases, such genomic loci do not need to be informative in terms of genotype since copy number is determined by hybridization intensities and doesn't depend on the genotype. Also, copy number abnormalities can be detected using methods that do not use SNPs, such as, for example, array CGH using BAC, cDNA and/or oligonucleotide arrays.

For example, methods for evaluating copy number of nucleic acid in a sample include, but are not limited to, hybridization-based assays. One method for evaluating the copy number of encoding nucleic acid in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal mRNA (e.g., a non-amplified portion of the same or related cell, tissue, organ, etc.) provides an estimate of the relative copy number of the target nucleic acid. Similar methods for determining copy number can be performed using transcriptional arrays, which are well-known in the art.

An alternative means for determining the copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

Preferred hybridization-based assays include, but are not limited to, traditional "direct probe" methods such as Southern blots or in situ hybridization (e.g., FISH and FISH plus SKY), and "comparative probe" methods such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters. Preferred probes are sufficiently long so as to specifically hybridize with the target nucleic acid(s) under stringent conditions. The preferred size range is from about 200 bases to about 1000 bases.

In some applications it is necessary to block the hybridization capacity of repetitive sequences. Thus, in some embodiments, tRNA, human genomic DNA, or Cot-I DNA is used to block non-specific hybridization.

In CGH methods, a first collection of nucleic acids (e.g., from a sample, e.g., a possible tumor) is labeled with a first label, while a second collection of nucleic acids (e.g., a control, e.g., from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Hybridization protocols suitable for use with the methods of the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc. In one embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

The methods of the invention are particularly well suited to array-based hybridization formats. Array-based CGH is described in U.S. Pat. No. 6,455,258, the contents of which are incorporated herein by reference.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR anlaysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989)*Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

In still other embodiments of the methods provided herein, separate sequencing of individual nucleic molecules (or their amplification products) is performed, as an alternative to hybridization-based assays, using nucleic acid sequencing techniques. In one embodiment, a high throughput parallel sequencing technique that isolates single nucleic acid molecules of a population of nucleic acid molecules prior to sequencing is used. Such strategies use so-called "next generation sequencing systems" including, without limitation, sequencing machines and/or strategies well known in the art, such as those developed by Illumina/Solexa (the Genome Analyzer; Bennett et al. (2005) Pharmacogenomics, 6:373-382), by Applied Biosystems, Inc. (the SOLiD Sequencer; solid.appliedbiosystems.com), by Roche (e.g., the 454 GS FLX sequencer; Margulies et al. (2005) Nature, 437:376-380; U.S. Pat. Nos. 6,274,320; 6,258,568; 6,210,891), by Heliscope™ system from Helicos Biosciences (see, e.g., U.S. Patent App. Pub. No. 2007/0070349), and by others. All of the copy number determining strategies described herein can similarly be applied to any of other nucleic acid-based analysis described herein, such as for informative loci and the like described further below.

In other embodiments, SNPs can be scored for heterozygosity or absence of heterozygosity. Techniques like major copy proportion analysis utilize the allelic-imbalance and copy number information to extend the analyses that can be performed with copy number of LOH events alone since they can involve copy number deletion, neutral, or gain events.

In other embodiments, to determine the GCAS of a cancer in a subject, heterozygous SNPs located throughout the genome are identified using nucleic acid samples derived from non-cancerous tissue of the subject or a population of subjects of a single species, and the number is determined of those heterozygous SNPs identified that maintain heterozygosity (or alternatively do not exhibit heterozygosity, i.e., have lost heterozygosity) in a nucleic acid sample of, or derived from, genomic DNA of cancerous tissue of the subject. A nucleic acid sample "derived from" genomic DNA includes but is not limited to pre-messenger RNA (containing introns), amplification products of genomic DNA or pre-messenger RNA, fragments of genomic DNA optionally with adapter oligonucleotides ligated thereto or present in cloning or other vectors, etc. (introns and non-coding regions should not be selectively removed).

All of the SNPs known to exhibit heterozygosity in the species to which the subject with cancer belongs, need not be included in the number of heterozygous SNPs used. In some embodiments, at least 250, 500, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 50,000, 60,000, 70,000, 80,000, 90,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000 SNPs or more, or any range in between, or other informative loci of interest (e.g., RFLPs, STRs, etc.) are used. Preferably, such SNPs are in the human genome. In one embodiment, the plurality of heterozygous SNPs are randomly distributed throughout the genome at least every 1, 5, 10, 50, 100, 250, 500, 1,000, 1,500, 2,000, 2,500, 3,000, 5,000, 10,000 kb or more, or any range in between. By "randomly distributed," as used above, is meant that the SNPs of the plurality are not selected by bias toward any specific chromosomal locus or loci; however, other biases (e.g., the avoidance of repetitive DNA sequences) can be used in the selection of the SNPs. In other embodiments, the plurality of heterozygous SNPs are not randomly distributed throughout the genome (i.e., distributed within at least 250, 500, 1,000, 1,500, 2,000, 2,500, 3,000, 5,000, 10,000, 11,000, 12,000, 13,000, 14,000, 15,000, 16,000, 17,000, 18,000, 19,000, 20,000, 21,000, 22,000, 23,000, 24,000, or 25,000 kb=25 Mb). Such regions can further be biased, in some embodiments, to specific chromosomal regions such as telomeres defined as regions extending toward the telomere but not crossing the centromere. In one embodiment, the telomeric allelic imbalance segment size is at least 1 Mb, 2 Mb, 3 Mb, 4 Mb, 5 Mb, 6 Mb, 7 Mb, 8 Mb, 9 Mb, 10 Mb, 11 Mb, 12 Mb, 13 Mb, 14 Mb, 15 Mb, 16 Mb, 17 Mb, 18 Mb, 19 Mb, 20 Mb, 21 Mb, 22 Mb, 23 Mb, 24 Mb, 25 Mb, or more, or any range in between, such as between 5 and 25 Mb. In another embodiment, the telomeric allelic imbalance segment size is 12 Mb. By contrast, interstitial regions do not involve the telomere. Interstitial regions are defined herein as regions of allelic imbalance that start downstream of the telomere meaning that there is at least some part of the chromosome with no allelic imbalance between the telomere and the region of allelic imbalance.. In one embodiment, the plurality of heterozygous SNPs is not found in regions of genomic DNA that are repetitive. In another embodiment, the plurality of heterozygous SNPs comprises SNPs located in the genome on different chromosomal loci, wherein the different chromosomal loci comprise loci on each of the chromosomes of the species, or on each arm of each chromosome of the species (e.g., telomeric region thereof).

Heterozygous SNPs can be used in the methods of the invention to determine the phenotype of a cancer are informative, meaning heterozygosity is observed in the nucleic acid sample from non-cancerous tissue and/or cells of a subject. According to the methods of the invention, these informative SNPs are examined in the nucleic acid sample from a cancerous tissue and/or cells of a subject to determine GCAS.

In a further embodiment, the nucleic acid samples used to determine the number of heterozygous SNPs in the plurality of SNPs, that exhibit heterozygosity in genomic DNA of non-cancerous tissue of the species to which the cancer patient belongs, are taken from at least 1, 2, 5, 10, 20, 30, 40, 50, 100, or 250 different organisms of that species. A skilled artisan will understand that appropriate controls can be determined based upon the average frequency of SNP alleles that exist within the same ethnic group of the species to which the patient belongs.

In certain embodiments, the informative SNPs used in the methods of the invention to determine and/or predict the phenotype of a cancer comprise at least one SNP on each chromosome of a subject (e.g., a telomeric region of each chromosome). In a related embodiment, the informative SNPs used in the methods of the invention to determine and/or predict the phenotype of a cancer comprise at least one SNP on each arm of each chromosome of a subject (e.g., a telomeric region of each arm of each chromosome).

II. Prediction of Response to Therapy

In certain embodiments, the invention provides methods for determining the phenotype of a cancer wherein the phenotype is response to therapy. The therapy may be any anti-cancer therapy including, but not limited to, chemotherapy, radiation therapy, immunotherapy, small molecule inhibitors, shRNA, hormonal, and combinations thereof.

Where GCAS represents copy deletions, copy gains, whole chromosome losses, whole chromosome gains and/or loss of heterozygosity, subjects whose cancerous tissue exhibit a GCAS below a threshold value are predicted to have a poorer response to therapy (e.g., radiation or chemotherapy) than those with high GCAS (above the threshold value). Where GCAS represents lack of copy or chromosome number changes and/or retention of heterozygosity, subjects whose cancerous tissue exhibits a GCAS above a threshold value are predicted to have a poorer response to therapy (e.g., radiation or chemotherapy) than those with low GCAS (below the threshold value).

By way of explanation, but without being bound by theory, it is believed that where the GCAS value represents loss of heterozygosity or allelic imabalance, it identifies cells harboring improperly repaired chromosomal DNA double-strand breaks and the genome-wide count of these chromosomal rearrangements in a specific tumor indicates the degree of DNA repair incompetence, independent of the specific causative DNA repair defect. In such subjects, the total number of chromosomal rearrangements in a tumor indicates the inability to repair DNA damage induced by anti-cancer therapies, and consequently predicts sensitivity to such anti-cancer therapies. Also by way of explanation and without being bound by theory, it is believed that GCAS representing copy gains may indicate genetic defects other than or in addition to DNA repair defects and that GCAS representing whole chromosome loss or gain may indicate mitotic checkpoint defects or chromosome segregation defects, and the like. Such aberrations in faithful DNA repair, segregation, check point control, etc. has been determined to be predictive of the cells harboring such aberrations to treatment with anti-cancer therapies (e.g., chemotherapeutics) in subjects.

The response to anti-cancer therapies relates to any response of the tumour to chemotherapy, preferably to a change in tumour mass and/or volume after initiation of neoadjuvant or adjuvant chemotherapy. Tumor response may be assessed in a neoadjuvant or adjuvant situation where the size of a tumour after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumour after biopsy or surgical resection. Response may be recorded in a quantitative fashion like percentage change in tumour volume or cellularity or using a semi-quantitative scoring system such as residual cancer burden (Symmans et al., J. Clin. Oncol. (2007) 25:4414-4422) or Miller-Payne score (Ogston et al., Breast (Edinburgh, Scotland) (2003) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumour cells and/or the tumour bed.

Additional criteria for evaluating the response to anti-cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-cancer therapeutic regimen can be administered to a population of subjects and the outcome can be correlated to GCAS's that were determined prior to administration of any anti-cancer therapy. The outcome measurement may be pathologic response to therapy given in the neo-adjuvant setting. Alternatively, outcome measures, such as overall survival and disease-free survival can be monitored over a period of time for subjects following anti-cancer therapy for whom GCAS values are known. In certain embodiments, the same doses of anti-cancer agents are administered to each subject. In related embodiments, the doses administered are standard doses known in the art for anti-cancer agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. GCAS threshold values that correlate to outcome of an anti-cancer therapy can be determined using methods such as those described in the Example section.

III. Anti-Cancer Therapeutic Agents

The efficacy of anti-cancer therapies which damage DNA, as well as agents that take advantage of DNA repair defects but do not damage DNA themselves, such as poly ADP ribose polymerase (PARP) inhibitors, as well as chemotherapy or radiation therapy, is predicted according to the GCAS level of a cancer in a subject according to the methods described herein.

In one embodiment, the efficacy of chemotherapies is predicted. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. No. Re. 36,397); and NU1025 (Bowman et al.). The foregoing examples of chemotherapeutic agents are illustrative, and are not intended to be limiting.

In a preferred embodiment, the chemotherapeutic agents are platinum compounds, such as cisplatin, carboplatin, oxaliplatin, nedaplatin, and iproplatin. Other antineoplastic platinum coordination compounds are well known in the art, can be modified according to well known methods in the art, and include the compounds disclosed in U.S. Pat. Nos. 4,996,337, 4,946,954, 5,091,521, 5,434,256, 5,527,905, and 5,633,243, all of which are incorporated herein by reference.

In another embodiment, GCAS predicts efficacy of radiation therapy. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

Anti-cancer therapies which damage DNA to a lesser extent than chemotherapy or radiation therapy may have efficacy in subjects determined to have relatively lower or higher GCAS determinations using the methods of the invention for determining the phenotype of a cancer. Examples of such therapies include immunotherapy, hormone therapy, and gene therapy. Such therapies include, but are not limited to, the use of antisense polynucleotides, ribozymes, RNA interference molecules, triple helix polynucleotides and the like, where the nucleotide sequence of such compounds are related to the nucleotide sequences of DNA and/or RNA of genes that are linked to the initiation, progression, and/or pathology of a tumor or cancer. For example, oncogenes, growth factor genes, growth factor receptor genes, cell cycle genes, DNA repair genes, and others, may be used in such therapies.

Immunotherapy may comprise, for example, use of cancer vaccines and/or sensitized antigen presenting cells. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines.

Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In one embodiment, anti-cancer therapy used for cancers whose phenotype is determined by the methods of the invention can comprise one or more types of therapies described herein including, but not limited to, chemotherapeutic agents, immunotherapeutics, anti-angiogenic agents, cytokines, hormones, antibodies, polynucleotides, radiation and photodynamic therapeutic agents. For example, combination therapies can comprise one or more chemotherapeutic agents and radiation, one or more chemotherapeutic agents and immunotherapy, or one or more chemotherapeutic agents, radiation and chemotherapy.

The duration and/or dose of treatment with anti-cancer therapies may vary according to the particular anti-cancer agent or combination thereof. An appropriate treatment time for a particular cancer therapeutic agent will be appreciated by the skilled artisan. The invention contemplates the continued assessment of optimal treatment schedules for each cancer therapeutic agent, where the phenotype of the cancer of the subject as determined by the methods of the invention is a factor in determining optimal treatment doses and schedules.

IV. Cancers for which Phenotype can be Determined

The methods of the invention can be used to determine the phenotype of many different cancers. Specific examples of types of cancers for which the phenotype can be determined by the methods encompassed by the invention include, but are not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In some embodiments, the cancer whose phenotype is determined by the method of the invention is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated.

V. Subjects

In one embodiment, the subject for whom predicted efficacy of an anti-cancer therapy is determined, is a mammal (e.g., mouse, rat, primate, non-human mammal, domestic animal such as dog, cat, cow, horse), and is preferably a human.

In another embodiment of the methods of the invention, the subject has not undergone chemotherapy or radiation therapy. In alternative embodiments, the subject has undergone chemotherapy or radiation therapy (e.g., such as with cisplatin, carboplatin, and/or taxane). In related embodiments, the subject has not been exposed to levels of radiation or chemotoxic agents above those encountered generally or on average by the subjects of a species.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

According to one aspect of the invention, GCAS can be used to determine the phenotype, i.e. responsivenes to therapy of a cancer in a subject, where the subject has previously undergone chemotherapy, radiation therapy, or has been exposed to radiation, or a chemotoxic agent. Such therapy or exposure could potentially damage DNA and alter the numbers of informative heterozygous SNPs in a subject. The altered number of informative heterozygous SNPs would in turn alter the GCAS of a subject. Because the non-cancerous DNA samples would exhibit greater or fewer heterozygous SNPs, the range of GCASs would be altered for a population of subjects. In certain embodiments, DNA damage from therapy or exposure in a subject or population of subjects occurs about 1 month, 2 months, 3 months, 4 months, 5 months, 6 months, 7 months, 8 months, 9 months, 10 months, 11 months, 1 year, 1.5 years, 2 years or more before determination of GCAS.

To determine GCAS threshold values for subjects that exhibit DNA damage from therapy or exposure, a population of subjects is monitored who have had chemotherapy or radiation therapy, preferably via identical or similar treatment regimens, including dose and frequency, for said subjects.

VI. Nucleic Acid Sample Preparation

A. Nucleic Acid Isolation

Nucleic acid samples derived from cancerous and non-cancerous cells of a subject that can be used in the methods of the invention to determine the phenotype of a cancer can be prepared by means well known in the art. For example, surgical procedures or needle biopsy aspiration can be used to collect cancerous samples from a subject. In some embodiments, it is important to enrich and/or purify the cancerous tissue and/or cell samples from the non-cancerous tissue and/or cell samples. In other embodiments, the cancerous tissue and/or cell samples can then be microdissected to reduce amount of normal tissue contamination prior to extraction of genomic nucleic acid or pre-RNA for use in the methods of the invention. In still another embodiment, the cancerous tissue and/or cell samples are enriched for cancer cells by at least 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range in between, in cancer cell content. Such enrichment can be accomplished according to methods well-known in the art, such as needle microdissection, laser microdissection, fluorescence activated cell sorting, and immunological cell sorting. In one embodiment, an automated machine performs the hyperproliferative cell enrichment to thereby transform the biological sample into a purified form enriched for the presence of hyperproliferative cells.

Collecting nucleic acid samples from non-cancerous cells of a subject can also be accomplished with surgery or aspiration. In surgical procedures where cancerous tissue is removed, surgeons often remove non-cancerous tissue and/or cell samples of the same tissue type of the cancer patient for comparison. Nucleic acid samples can be isolated from such non-cancerous tissue of the subject for use in the methods of the invention.

In certain embodiments of the methods of the invention, nucleic acid samples from non-cancerous tissues are not derived from the same tissue type as the cancerous tissue and/or cells sampled, and/or are not derived from the cancer patient. The nucleic acid samples from non-cancerous tissues may be derived from any non-cancerous and/or disease-free tissue and/or cells. Such non-cancerous samples can be collected by surgical or non-surgical procedures. In certain embodiments, non-cancerous nucleic acid samples are derived from tumor-free tissues. For example, non-cancerous samples may be collected from lymph nodes, peripheral blood lymphocytes, and/or mononuclear blood cells, or any subpopulation thereof. In a preferred embodiment, the non-cancerous tissue is not pre-cancerous tissue, e.g., it does not exhibit any indicia of a pre-neoplastic condition such as hyperplasia, metaplasia, or dysplasia.

In one embodiment, the nucleic acid samples used to compute GCAS (e.g., the number of heterozygous SNPs in the plurality of total SNPs that exhibit heterozygosity in genomic DNA of non-cancerous tissue of the species to which the cancer patient belongs) are taken from at least 1, 2, 5, 10, 20, 30, 40, 50, 100, or 200 different organisms of that species.

According to certain aspects of the invention, nucleic acid "derived from" genomic DNA, as used in the methods of the invention, e.g., in hybridization experiments to determine heterozygosity of SNPs, can be fragments of genomic nucleic acid generated by restriction enzyme digestion and/or ligation to other nucleic acid, and/or amplification products of genomic nucleic acids, or pre-messenger RNA (pre-mRNA), amplification products of pre-mRNA, or genomic DNA fragments grown up in cloning vectors generated, e.g., by "shotgun" cloning methods. In certain embodiments, genomic nucleic acid samples are digested with restriction enzymes.

B. Amplification of Nucleic Acids

Though the nucleic acid sample need not comprise amplified nucleic acid, in some embodiments, the isolated nucleic acids can be processed in manners requiring and/or taking advantage of amplification. The genomic DNA samples of a subject optionally can be fragmented using restriction endonucleases and/or amplified prior to determining GCAS. In one embodiment, the DNA fragments are amplified using polymerase chain reaction (PCR). Methods for practicing PCR are well known to those of skill in the art. One advantage of PCR is that small quantities of DNA can be used. For example, genomic DNA from a subject may be about 150 ng, 175, ng, 200 ng, 225 ng, 250 ng, 275 ng, or 300 ng of DNA.

In certain embodiments of the methods of the invention, the nucleic acid from a subject is amplified using a single primer pair. For example, genomic DNA samples can be digested with restriction endonucleases to generate fragments of genomic DNA that are then ligated to an adaptor DNA sequence which the primer pair recognizes. In other embodiments of the methods of the invention, the nucleic acid of a subject is amplified using sets of primer pairs specific to loci of interest (e.g., RFLPs, STRs, SNPs, etc.) located throughout the genome. Such sets of primer pairs each recognize genomic DNA sequences flanking particular loci of interest (e.g., SNPs, RFLPs, STRs, etc.). A DNA sample suitable for hybridization can be obtained, e.g., by polymerase chain reaction (PCR) amplification of genomic DNA, fragments of genomic DNA, fragments of genomic DNA ligated to adaptor sequences or cloned sequences. Computer programs that are well known in the art can be used in the design of primers with the desired specificity and optimal amplification properties, such as Oligo version 5.0 (National Biosciences). PCR methods are well known in the art, and are described, for example, in Innis et al., eds., 1990, PCR Protocols: A Guide to Methods And Applications, Academic Press Inc., San Diego, Calif. It will be apparent to one skilled in the art that controlled robotic systems are useful for isolating and amplifying nucleic acids and can be used.

In other embodiments, where genomic DNA of a subject is fragmented using restriction endonucleases and amplified prior to determining GCAS, the amplification can comprise cloning regions of genomic DNA of the subject. In such methods, amplification of the DNA regions is achieved through the cloning process. For example, expression vectors can be engineered to express large quantities of particular fragments of genomic DNA of the subject (Sambrook, J. et al., eds., 1989, Molecular Cloning: A Laboratory Manual, 2nd Ed., Cold Spring Harbor Laboratory Press, Cold Spring Harbor, N.Y., at pp. 9.47-9.51).

In yet other embodiments, where the DNA of a subject is fragmented using restriction endonucleases and amplified prior to determining GCAS, the amplification comprises expressing a nucleic acid encoding a gene, or a gene and flanking genomic regions of nucleic acids, from the subject. RNA (pre-messenger RNA) that comprises the entire transcript including introns is then isolated and used in the methods of the invention to determine GCAS and the phenotype of a cancer.

In certain embodiments, no amplification is required. In such embodiments, the genomic DNA, or pre-RNA, of a subject may be fragmented using restriction endonucleases or other methods. The resulting fragments may be hybridized to SNP probes. Typically, greater quantities of DNA are needed to be isolated in comparison to the quantity of DNA or pre-mRNA needed where fragments are amplified. For example, where the nucleic acid of a subject is not amplified, a DNA sample of a subject for use in hybridization may be about 400 ng, 500 ng, 600 ng, 700 ng, 800 ng, 900 ng, or 1000 ng of DNA or greater. Alternatively, in other embodiments, methods are used that require very small amounts of nucleic acids for analysis, such as less than 400 ng, 300 ng, 200 ng, 100 ng, 90 ng, 85 ng, 80 ng, 75 ng, 70 ng, 65 ng, 60 ng, 55 ng, 50 ng, or less, such as is used for molecular inversion probe (MIP) assays. These techniques are particularly useful for analyzing clinical samples, such as paraffin embedded formalin-fixed material or small core needle biopsies, characterized as being readily available but generally having reduced DNA quality (e.g., small, fragmented DNA) and/or not providing large amounts of nucleic acids.

C. Hybridization

The nucleic acid samples derived from a subject used in the methods of the invention can be hybridized to arrays comprising probes (e.g., oligonucleotide probes) in order to identify informative loci of interest (e.g., SNPs, RFLPs, STRs, etc.). Hybridization can also be used to determine whether the informative loci of interest (e.g., SNPs, RFLPs, STRs, etc.) identified exhibit chromosomal aberrations (e.g., allelic imbalance, loss of heterozygosity, total copy number change, copy number gain, and copy number loss) in nucleic acid samples from cancerous tissues and/or cells of the subject. In preferred embodiments, the probes used in the methods of the invention comprise an array of probes that can be tiled on a DNA chip (e.g., SNP oligonucleotide probes). In some embodiments, heterozygosity of a SNP locus is determined by a method that does not comprise detecting a change in size of restriction enzyme-digested nucleic acid fragments. In other embodiments, SNPs are analyzed to identify allelic imbalance.

Hybridization and wash conditions used in the methods of the invention are chosen so that the nucleic acid samples to be analyzed by the invention specifically bind or specifically hybridize to the complementary oligonucleotide sequences of the array, preferably to a specific array site, wherein its complementary DNA is located. In some embodiments, the complementary DNA can be completely matched or mismatched to some degree as used, for example, in Affymetrix oligonucleotide arrays such as those used to analyze SNPs in MIP assays.

The single-stranded synthetic oligodeoxyribonucleic acid DNA probes of an array may need to be denatured prior to contact with the nucleic acid samples from a subject, e.g., to remove hairpins or dimers which form due to self complementary sequences.

Optimal hybridization conditions will depend on the length of the probes and type of nucleic acid samples from a subject. General parameters for specific (i.e., stringent) hybridization conditions for nucleic acids are described in Sambrook, J. et al., eds., 1989, Molecular Cloning: A Laboratory Manual, 2nd Ed., Cold Spring Harbor Laboratory Press, Cold Spring Harbor, N.Y., at pp. 9.47-9.51 and 11.55-11.61; Ausubel et al., eds., 1989, Current Protocols in Molecules Biology, Vol. 1, Green Publishing Associates, Inc., John Wiley & Sons, Inc., New York, at pp. 2.10.1-2.10.16. Exemplary useful hybridization conditions are provided in, e.g., Tijessen, 1993, Hybridization With Nucleic Acid Probes, Elsevier Science Publishers B. V. and Kricka, 1992, Nonisotopic DNA Probe Techniques, Academic Press, San Diego, Calif.

D. Oligonucleotide Nucleic Acid Arrays

In some embodiments of the methods of the present invention, DNA arrays can be used to determine whether nucleic acid samples exhibit chromosomal aberrations (e.g., allelic imbalance, loss of heterozygosity, total copy number change, copy number gain, and copy number loss) by measuring the level of hybridization of the nucleic acid sequence to oligonucleotide probes that comprise complementary sequences. Hybridization can be used to determine the presence or absence of heterozygosity. Various formats of DNA arrays that employ oligonucleotide "probes," (i.e., nucleic acid molecules having defined sequences) are well known to those of skill in the art.

Typically, a set of nucleic acid probes, each of which has a defined sequence, is immobilized on a solid support in such a manner that each different probe is immobilized to a predetermined region. In certain embodiments, the set of probes forms an array of positionally-addressable binding (e.g., hybridization) sites on a support. Each of such binding sites comprises a plurality of oligonucleotide molecules of a probe bound to the predetermined region on the support. More specifically, each probe of the array is preferably located at a known, predetermined position on the solid support such that the identity (i.e., the sequence) of each probe can be determined from its position on the array (i.e., on the support or surface). Microarrays can be made in a number of ways, of which several are described herein. However produced, microarrays share certain characteristics, they are reproducible, allowing multiple copies of a given array to be produced and easily compared with each other.

Preferably, the microarrays are made from materials that are stable under binding (e.g., nucleic acid hybridization) conditions. The microarrays are preferably small, e.g., between about 1 cm$^2$ and 25 cm$^2$, preferably about 1 to 3 cm$^2$. However, both larger and smaller arrays are also contemplated and may be preferable, e.g., for simultaneously evaluating a very large number of different probes.

Oligonucleotide probes can be synthesized directly on a support to form the array. The probes can be attached to a solid support or surface, which may be made, e.g., from glass, plastic (e.g., polypropylene, nylon), polyacrylamide, nitrocellulose, gel, or other porous or nonporous material. The set of immobilized probes or the array of immobilized probes is contacted with a sample containing labeled nucleic acid species so that nucleic acids having sequences complementary to an immobilized probe hybridize or bind to the probe. After separation of, e.g., by washing off, any unbound material, the bound, labeled sequences are detected and measured. The measurement is typically conducted with computer assistance. Using DNA array assays, complex mixtures of labeled nucleic acids, e.g., nucleic acid fragments derived a restriction digestion of genomic DNA from non-cancerous tissue, can be analyzed. DNA array technologies have made it possible to determine heterozygosity of a large number of informative loci of interest (e.g., SNPs, RFLPs, STRs, etc.) throughout the genome.

In certain embodiments, high-density oligonucleotide arrays are used in the methods of the invention. These arrays containing thousands of oligonucleotides complementary to defined sequences, at defined locations on a surface can be synthesized in situ on the surface by, for example, photolithographic techniques (see, e.g., Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; 5,510,270; 5,445,934; 5,744,305; and 6,040,138). Methods for generating arrays using inkjet technology for in situ oligonucleotide synthesis are also known in the art (see, e.g., Blanchard, International Patent Publication WO 98/41531, published Sep. 24, 1998; Blanchard et al., 1996, Biosensors And Bioelectronics 11:687-690; Blanchard, 1998, in Synthetic DNA Arrays in Genetic Engineering, Vol. 20, J. K. Setlow, Ed., Plenum Press, New York at pages 111-123). Another method for attaching the nucleic acids to a surface is by printing on glass plates, as is described generally by Schena et al. (1995, Science 270:467-470). Other methods for making microarrays, e.g., by masking (Maskos and Southern, 1992, Nucl. Acids. Res. 20:1679-1684), may also be used. When these methods are used, oligonucleotides (e.g., 15 to 60-mers) of known sequence are synthesized directly on a surface such as a derivatized glass slide. The array produced can be redundant, with several oligonucleotide molecules corresponding to each informative locus of interest (e.g., SNPs, RFLPs, STRs, etc.).

One exemplary means for generating the oligonucleotide probes of the DNA array is by synthesis of synthetic polynucleotides or oligonucleotides, e.g., using N-phosphonate or phosphoramidite chemistries (Froehler et al., 1986, Nucleic Acid Res. 14:5399-5407; McBride et al., 1983, Tetrahedron Lett. 24:246-248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, Nature 363:566-568; U.S. Pat. No. 5,539,083). In alternative embodiments, the hybridization sites (i.e., the probes) are made from plasmid or phage clones of regions of genomic DNA corresponding to SNPs or the complement thereof.

The size of the oligonucleotide probes used in the methods of the invention can be at least 10, 20, 25, 30, 35, 40, 45, or 50 nucleotides in length. It is well known in the art that although hybridization is selective for complementary sequences, other sequences which are not perfectly complementary may also hybridize to a given probe at some level. Thus, multiple oligonucleotide probes with slight variations can be used, to optimize hybridization of samples. To further optimize hybridization, hybridization stringency condition, e.g., the hybridization temperature and the salt concentrations, may be altered by methods that are well known in the art.

In preferred embodiments, the high-density oligonucleotide arrays used in the methods of the invention comprise oligonucleotides corresponding to informative loci of interest (e.g., SNPs, RFLPs, STRs, etc.). The oligonucleotide probes may comprise DNA or DNA "mimics" (e.g., derivatives and analogues) corresponding to a portion of each informative locus of interest (e.g., SNPs, RFLPs, STRs, etc.) in a subject's genome. The oligonucleotide probes can be modified at the base moiety, at the sugar moiety, or at the phosphate backbone. Exemplary DNA mimics include, e.g., phosphorothioates. For each SNP locus, a plurality of different oligonucleotides may be used that are complementary to the sequences of sample nucleic acids. For example, for a single informative locus of interest (e.g., SNPs, RFLPs, STRs, etc.) about 2, 3, 4, 5, 6, 7, 8,9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more different oligonucleotides can be used. Each of the oligonucleotides for a particular informative locus of interest may have a slight variation in perfect matches, mismatches, and flanking sequence around the SNP. In certain embodiments, the probes are generated such that the probes for a particular informative locus of interest comprise overlapping and/or successive overlapping sequences which span or are tiled across a genomic region containing the target site, where all the probes contain the target site. By way of example, overlapping probe sequences can be tiled at steps of a predetermined base intervals, e. g. at steps of 1, 2, 3, 4, 5, 6, 7, 8, 9, or 10 bases intervals.

In certain embodiments, the assays can be performed using arrays suitable for use with molecular inversion probe protocols such as described by Wang et al. (2007) *Genome Biol.* 8, R246.

For oligonucleotide probes targeted at nucleic acid species of closely resembled (i.e., homologous) sequences, "cross-hybridization" among similar probes can significantly contaminate and confuse the results of hybridization measurements. Cross-hybridization is a particularly significant concern in the detection of SNPs since the sequence to be detected (i.e., the particular SNP) must be distinguished from other sequences that differ by only a single nucleotide. Cross-hybridization can be minimized by regulating either the hybridization stringency condition and/or during post-hybridization washings. Highly stringent conditions allow detection of allelic variants of a nucleotide sequence, e.g., about 1 mismatch per 10-30 nucleotides.

There is no single hybridization or washing condition which is optimal for all different nucleic acid sequences. For particular arrays of informative loci of interest, these conditions can be identical to those suggested by the manufacturer or can be adjusted by one of skill in the art.

In preferred embodiments, the probes used in the methods of the invention are immobilized (i.e., tiled) on a glass slide called a chip. For example, a DNA microarray can comprises a chip on which oligonucleotides (purified single-stranded DNA sequences in solution) have been robotically printed in an (approximately) rectangular array with each spot on the array corresponds to a single DNA sample which encodes an oligonucleotide. In summary the process comprises, flooding the DNA microarray chip with a labeled sample under conditions suitable for hybridization to occur between the slide sequences and the labeled sample, then the array is washed and dried, and the array is scanned with a laser microscope to detect hybridization. In certain embodiments there are at least 250, 500, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000,34,000, 35,000, 36,000, 37,000, 38,000, 39,000, 40,000, 41,000, 42,000, 43,000, 44,000, 45,000, 50,000, 60,000, 70,000, 80,000, 90,000, 100,000 or more or any range in between, of informative loci of interest for which probes appear on the array (with match/mismatch probes for a single locus of interest or probes tiled across a single locus of interest counting as one locus of interest). The maximum number of informative loci of interest being probed per array is determined by the size of the genome and genetic diversity of the subjects species. DNA chips are well known in the art and can be purchased in pre-fabricated form with sequences specific to particular species. In some embodiments, the Genome-Wide Human SNP Array 6.0™ and/or the 50K XbaI arrays (Affymetrix, Santa Clara, Calif.) are used in the methods of the invention. In other embodiments, SNPs and/or DNA copy number can be detected and quantitated using sequencing methods, such as "next-generation sequencing methods" as described further above.

E. Signal Detection

In some embodiments, nucleic acid samples derived from a subject are hybridized to the binding sites of an array described herein. In certain embodiments, nucleic acid samples derived from each of the two sample types of a subject (i.e., cancerous and non-cancerous) are hybridized to separate, though identical, arrays. In certain embodiments, nucleic acid samples derived from one of the two sample types of a subject (i.e., cancerous and non-cancerous) is hybridized to such an array, then following signal detection the chip is washed to remove the first labeled sample and reused to hybridize the remaining sample. In other embodiments, the array is not reused more than once. In certain embodiments, the nucleic acid samples derived from each of the two sample types of a subject (i.e., cancerous and non-cancerous) are differently labeled so that they can be distinguished. When the two samples are mixed and hybridized to the same array, the relative intensity of signal from each sample is determined for each site on the array, and any relative difference in abundance of an allele of informative loci of interest detected.

Signals can be recorded and, in some embodiments, analyzed by computer. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the array, a ratio of the emission of the two fluorophores can be calculated, which may help in eliminating cross hybridization signals to more accurately determining whether a particular SNP locus is heterozygous or homozygous.

F. Labeling

In some embodiments, the nucleic acids samples, fragments thereof, or fragments thereof ligated to adaptor regions used in the methods of the invention are detectably labeled. For example, the detectable label can be a fluorescent label, e.g., by incorporation of nucleotide analogues. Other labels suitable for use in the present invention include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes.

Radioactive isotopes include that can be used in conjunction with the methods of the invention, but are not limited to, $^{32}P$ and $^{14}C$. Fluorescent molecules suitable for the present invention include, but are not limited to, fluorescein and its derivatives, rhodamine and its derivatives, texas red, 5'carboxy-fluorescein ("FAM"), 2', 7'-dimethoxy-4', 5'-dichloro-6-carboxy-fluorescein ("JOE"), N, N, N', N'-tetramethyl-6-carboxy-rhodamine ("TAMRA"), 6-carboxy-X-rhodamine ("ROX"), HEX, TET, IRD40, and IRD41.

Fluorescent molecules which are suitable for use according to the invention further include: cyamine dyes, including but not limited to Cy2, Cy3, Cy3.5, CY5, Cy5.5, Cy7 and FLUORX; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold.

Two-color fluorescence labeling and detection schemes may also be used (Shena et al., 1995, Science 270:467-470). Use of two or more labels can be useful in detecting variations due to minor differences in experimental conditions (e.g., hybridization conditions). In some embodiments of the invention, at least 5, 10, 20, or 100 dyes of different colors can be used for labeling. Such labeling would also permit analysis of multiple samples simultaneously which is encompassed by the invention.

The labeled nucleic acid samples, fragments thereof, or fragments thereof ligated to adaptor regions that can be used in the methods of the invention are contacted to a plurality of oligonucleotide probes under conditions that allow sample nucleic acids having sequences complementary to the probes to hybridize thereto.

Depending on the type of label used, the hybridization signals can be detected using methods well known to those of skill in the art including, but not limited to, X-Ray film, phosphor imager, or CCD camera. When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al. (1996) Genome Res. 6, 639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al. (1996) Genome Res. 6, 639-645. Alternatively, a fiber-optic bundle can be used such as that described by Ferguson et al. (1996) Nat. Biotech. 14, 1681-1684. The resulting signals can then be analyzed to determine the presence or absence of heterozygosity or homozygosity for informative loci of interest (e.g., SNPs, RFLPs, STRs, etc.) using computer software.

G. Algorithms for Analyzing Informative Loci of interest

Once the hybridization signal has been detected the resulting data can be analyzed using algorithms. In certain embodiments, the algorithm for determining heterozygosity at informative loci of interest (e.g., SNPs, RFLPs, STRs, etc.) is based on well known methods for calling allelic imbalance (AI), loss of heterozygosity (LOH), copy number aberrations (CNA), copy number gain (CNG), and copy number decrease (CND). For example, AI can be determined using major copy proportion (MCP) wherein AI for a given SNP is called, when the MCP value is greater than 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80. 0.81, 0.82, 0.83, 0.84, 0.85, 0.86, 0.87, 0.88, 0.89, 0.90, 0.91, 0.92, 0.92, 0.93, 0.94, 0.95, 0.96, 0.97, 0.98, or 0.99. Once calling is determined, enumeration methods can further be applied. For example, GCAS can be determined, for example, by: 1) the count of the total number of SNPs affected by AI or copy gain or LOH, 2) the count of the number of regions affected by AI (e.g., $N_{AI}$ as described further in the Examples; a single region is defined as a string of neighboring SNPs all showing AI bounded on at least one side by SNPs showing no AI/retention of heterozygosity. The region size is defined by the length of the chromosome represented by the string of SNPs with AI); 3) the count of the number of chromosomes with whole chromosome loss, or 4) the count of the number of chromosomal regions with CNA, CNG, CND, etc. Additional representative illustrations of such well known algorithms are provided in the Examples section below.

H. Computer Implementation Systems and Methods

In certain embodiments, the methods of the invention implement a computer program to calculate GCAS. For example, a computer program can be used to perform the algorithms described herein. A computer system can also store and manipulate data generated by the methods of the present invention which comprises a plurality of hybridization signal changes/profiles during approach to equilibrium in different hybridization measurements and which can be used by a computer system in implementing the methods of this invention. In certain embodiments, a computer system receives probe hybridization data; (ii) stores probe hybridization data; and (iii) compares probe hybridization data to determine the state of informative loci of interest in said nucleic acid sample from cancerous or pre-cancerous tissue. The GCAS is then calculated. In other embodiments, a computer system (i) compares the determined GCAS to a threshold value; and (ii) outputs an indication of whether said GCAS is above or below a threshold value, or a phenotype based on said indication. In certain embodiments, such computer systems are also considered part of the present invention.

Numerous types of computer systems can be used to implement the analytic methods of this invention according to knowledge possessed by a skilled artisan in the bioinformatics and/or computer arts.

Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; CRLMM software described in Silver et al. (2007) *Cell* 128, 991-1002; Aroma Affymetrix software described in Richardson et al. (2006) *Cancer Cell* 9, 121-132. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of hybridization signal profiles. Such stored profiles can be accessed and used to calculate GCAS. For example, of the hybridization signal profile of a sample derived from the non-cancerous tissue of a subject and/or profiles generated from population-based distributions of informative loci of interest in relevant populations of the same species were stored, it could then be compared to the hybridization signal profile of a sample derived from the cancerous tissue of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

Other embodiments of the present invention are described in the following Examples. The present invention is further illustrated by the following examples which should not be construed as further limiting.

EXAMPLES

Example 1

Materials and Methods For Example 2

Pathologic response after neoadjuvant cisplatin therapy in the TNBC cohort was measured using the semi-quantitative Miller-Payne scale as described (Silver et al. (2010) *J. Clin. Oncol.* 28, 1145-1153; Ogston et al. (2003) *Breast* 12, 320-327). MIP genotyping was performed as described (Wang et al. (2007) *Genome Biol.* 8, R246). Allele signal intensity and genotypes from MIP genotyping or public SNP array analyses were processed by the CRLMM algorithm (Lin et al. (2008) *Genome Biol.* 9, R63) as implemented in the R package "oligo". DNA copy number was determined using the R package "AromaAffymetrix" (Bengtsson et al. (2008) *Bioinformatics* 24, 759-767). Processed genotype data was exported to dChip (available on the world wide web at http://biosun1.harvard.edu/complab/dchip/) for major copy proportion (MCP) determination, defined as ratio of major copy number to major+minor copy number (Li et al. (2008) *Bioinformatics* 9, 204). An estimate of level of normal DNA contamination was made from the genomic MCP curve as described (Li et al. (2008) *Bioinformatics* 9, 204). Breast or ovarian cases estimated to have 75% or more tumor content were included in analyses. Allelic imbalance (AI) for specific purposes of the Examples described herein is defined as MCP>0.7 and regions of AI defined as more than 10 consecutive probes with AI. Telomeric AI for specific purposes of the Examples described herein is defined as AI regions that extend to telomere and do not cross the centromere. Association between $N_{tAI,12}$ and response to cisplatin in TNBC subjects was estimated by area under curve (AUC) of receiver operator characteristic (ROC) curve; p value is from two-sided Wilcoxon's rank test. Association between telomeric AI and time to recurrence of ovarian cancer after platinum therapy was estimated by Kaplan Meier analysis using a cutoff of 13 to define high $N_{tAI,12}$ group; p value is based on log-rank test. A complete listing of materials and methods is as follows:

A. Cell Lines and Drug Sensitivity Assays

Tripe-negative breast cancer cell lines BT20, BT549, HCC1187, HCC38, MDA-MB231 and MDA-MB468 were maintained at 37° C. with 5% $CO_2$ in RPMI 1640 medium and/or MEM medium supplemented with 10% FBS or other supplements as recommended by ATCC for each cell line. To test drug sensitivity, cells were exposed to a series of concentrations of cisplatin for 48 hours. Viable cell number was quantified using CellTiter 96 Aqueous One Solution Cell Proliferation Assay according to the manufacturer's instructions (Promega). The results are presented as the percentage of viable cells in drug-treated wells vs. media-treated control wells and plotted as a drug-does dependent cell survival curves (FIG. 1A). Drug sensitivity was quantified as the does of drug causing a 50% reduction of growth ($IC_{50}$). This data was originally generated for a separate study in which it was reported as "data not shown" in Li et al. (2010) *Nat. Med.* 16, 214-218.

B. Breast Cancer Cohort

A total of 28 mainly sporadic TNBC patients were treated with cisplatin monotherapy in the neo-adjuvant setting (Silver et al. (2010) *J. Clin. Oncol.* 28, 1145-1153). Cisplatin response was measured using the semiquantitative Miller-Payne score by pathological assessment of surgical samples after therapy (Ogston et al. (2003) *Breast* 12, 320-327). Pathologic complete response is equivalent to Miller-Payne score 5 and is defined as no residual invasive carcinoma in breast or lymph nodes.

C. Preparation of Breast Cancer Samples

A frozen core biopsy of the tumor was obtained before treatment started. Tumor tissue was available in the frozen core biopsy for 24 of 28 cases and in formalin fixed paraffin embedded diagnostic core biopsy samples from an additional 3 cases. Tumor cells were enriched by needle microdissection to remove stroma from hematoxylin and eosin (H & E) stained tissue sections. The remaining tissue on slides was examined by microscopy for estimation of enrichment. DNA was extracted from enriched tumor cells by proteinase K and RNase A digestions, phenol/chloroform extraction followed by ethanol precipitation. Adequate DNA for MIP genotyping analysis (minimum 80 ng) was obtained from all 27 cases for which tumor tissue was available. Paired normal DNA from each patient was obtained from peripheral blood lymphocytes.

D. Molecular inversion probe (MIP) genotyping analysis

DNA from breast tumor biopsy samples were sent to Affymetrix, Inc. (Santa Clara, Calif.) for MIP targeted genotyping analysis which generated allele signal intensity and genotypes for 42,000 individual single nucleotide polymorphisms (SNP). The complete MIP genotype data set is available on the NCBI GEO database.

E. Public Datasets

Affymetrix SNP 6.0 genomic profiles of six triple negative breast cancer cell lines, BT20, BT549, HCC1187, HCC38, MDA-MB231 and MDA-MB468, were acquired from the Welcome Trust Sanger Institute (information available on the world wide web at http://www.sanger.ac.uk/).

SNP data representing 118 ovarian carcinoma tumors arrayed on the Affymetrix 50K XbaI platform were acquired from the gene expression omnibus (GEO, GSE13813; Etemadmoghadam et al. (2009) *Clin. Cancer Res.* 15, 1417-1427). Of these, 38 tumors were of the serous subtype, had residual tumor after surgical debulking of less than 1 cm, and had received either adjuvant cisplatin or carboplatin treatment. Most patients (35 of 38) had also received taxane treatment.

F. Genotype and Copy Number Analysis

Allele signal intensity and genotypes from MIP genotyping or SNP array analyses were processed by the CRLMM algorithm (Lin et al. (2008) *Genome Biol.* 9, R63) as implemented in the R package "oligo". DNA copy number was determined using the R package "AromaAffymetrix" (Bengtsson et al. (2008) *Bioinformatics* 24, 759-767). Processed genotype data was exported to dChip (available on the world wide web at http://biosun1.harvard.edu/complab/dchip/) for major copy proportion (MCP) determination. MCP is defined as the ratio of the major allele copy number to the major+minor allele copy number (Li et al. (2008) *Bioinformatics* 9, 204). The degree of normal cell contamination was estimated by the degree of shift in the MCP curve of the majority of regions showing allelic imbalance across genome, excluding all regions of copy number gain (FIGS. 2B and 2C. The shift observed in the genomic MCP curves in paired normal and tumor cell line mixture experiments was used as reference to estimate normal contamination as described (Waddell et al. (2009) *Breast Cancer Res. Treat.* (December 4; e-published)). Accordingly, 21 of the 27 breast tumor samples and 33 of 38 of the ovarian cancer cases were estimated to have 25% or less of normal DNA contamination (≥75% tumor content) and were deemed acceptable for subsequent analysis.

Allelic imbalance (AI) was defined for purposes of the Examples described herein as MCP>0.70, which allows detection of the majority of loss of heterozygosity (LOH) events and of high-copy monoallelic amplifications in samples with 25% or less contamination or heterogeneity, but also excludes low-level copy gains (4-copy gains or less). Regions of AI were defined for purposes of the Examples described herein as more than 10 consecutive probes showing AI. In the TNBC dataset, the AI regions defined by these criteria included all callable LOH regions as determined from conventional genotype comparison. The total copy numbers (combining both alleles) were segmented by the circular binary segmentation algorithm. Eighty five percent of AI regions had total copy number near diploid or below, 9% of the AI regions showed total copy gain of 3, and 6% with total copy gain≥4. Thus, the identified AI regions predominantly represent LOH or uniparental chromosomal deletion.

Figure 3:
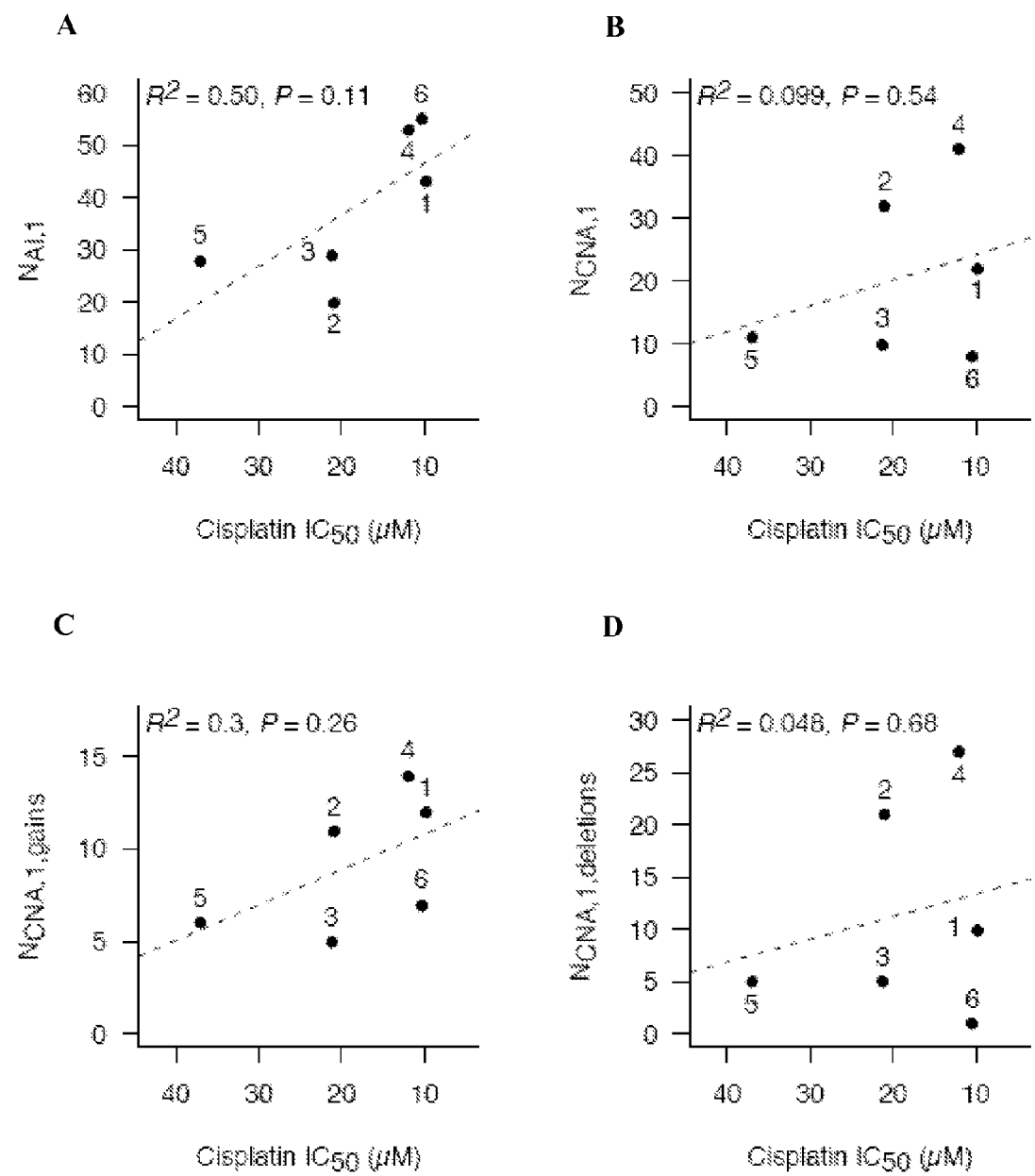
FIGS. 3A-3D show the association between cisplatin sensitivity and number of genomic abnormalities in a panel of TNBC cell lines.
Figure 5:
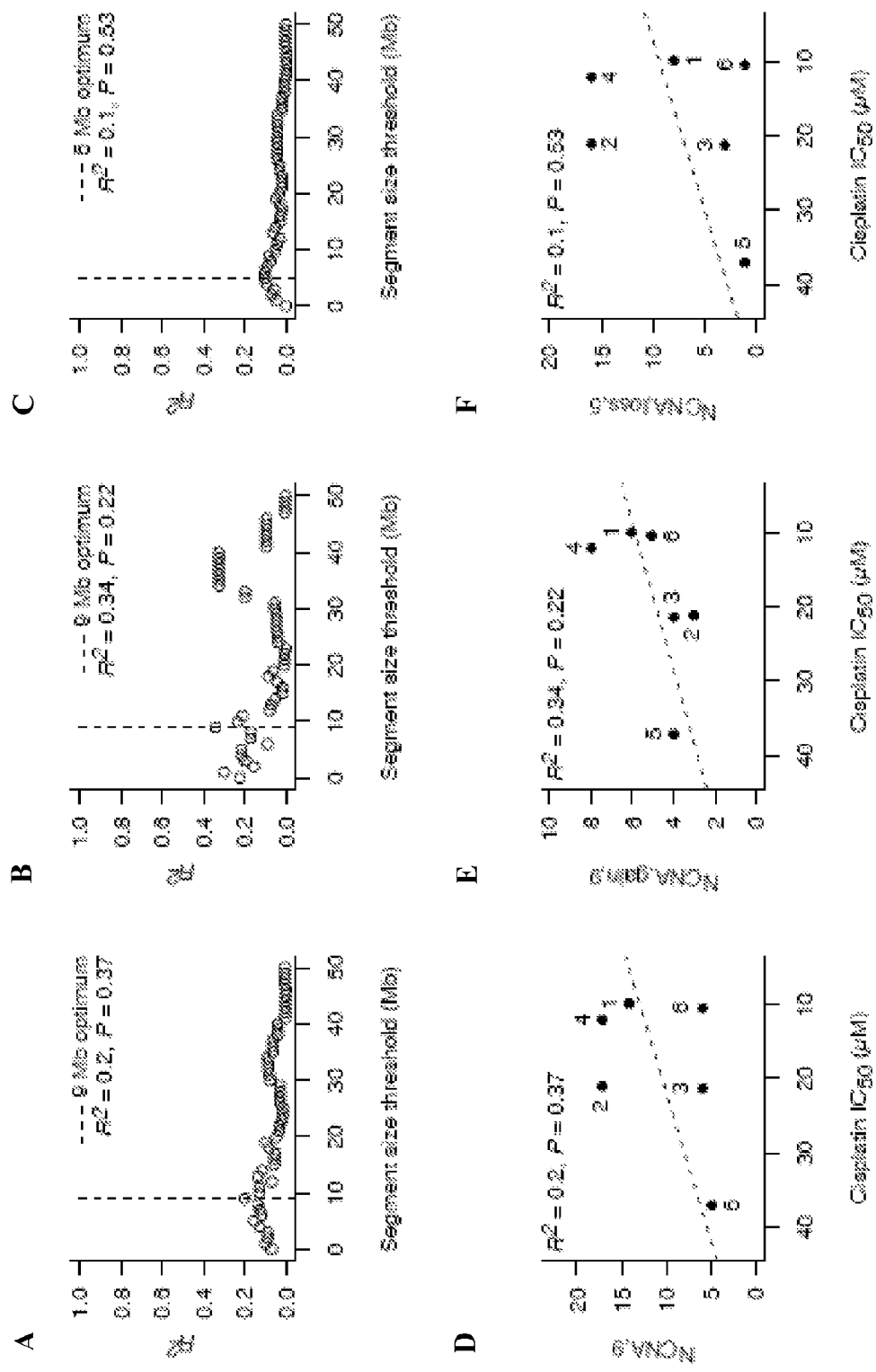
FIGS. 5A-5F show the association between enumerated copy number aberrations (CNA) and sensitivity to cisplatin in vitro.

G. Association Between Number of Genomic Aberrations and Platinum Sensitivity in vitro The numbers of regions of AI or regions with copy number aberration were compared to cell line-specific $IC_{50}$ values after applying a 1 Mb minimum size filter to remove very small regions that could be caused by noise in the SNP 6.0 data (FIG. 3). For comparison of telomeric and interstitial AI regions, telomeric AI was defined for purposes of the Examples described herein as AI that extends to the telomere but does not cross the centromere. Conversely, interstitial AI was defined for purposes of the Examples described herein as AI regions that do not involve the telomere. To investigate if there was an optimum minimum size of telomeric AI or copy number alteration segments that showed a superior correlation to the cisplatin $IC_{50}$, linear regression was used to compare the $IC_{50}$ values with the total number of segments larger than a certain threshold, which was increased by 1 Mb intervals between 0 and 100 Mb (FIG. 5).

H. Association Between Number of Telomeric AI Regions and Platinum Sensitivity in Tumors Total number of regions of telomeric AI was determined for each TNBC case with at least 75% tumor content. The optimal minimum telomeric AI segment size threshold of 12 Mb found in the cell lines were applied, and $N_{tAI,12}$ were counted for each subject. ROC (Receiver Operating Characteristic) curve analysis was performed to evaluate the capability of the total number of telomeric AI segments to predict pCR (Miller-Payne score 5) to cisplatin treatment. The association of $N_{tAI,12}$ with pCR to cisplatin was estimated by the area under the curve (AUC); the corresponding p-value is from two-sided Wilcoxon's rank test. Based on the ROC analysis, a $N_{tAI,12}$ of 13 resulted in 100% sensitivity for prediction of pCR in the TNBC cisplatin treated cohort.

The association between $N_{tAI,12}$ and time to recurrence after platinum-based therapy in the ovarian cancer cohort was estimated by Kaplan-Meier analysis with the "high $N_{tAI,12}$" group defined as at least 13 regions of $N_{tAI,12}$. P value is based on a log-rank test.

Example 2

Figure 2:
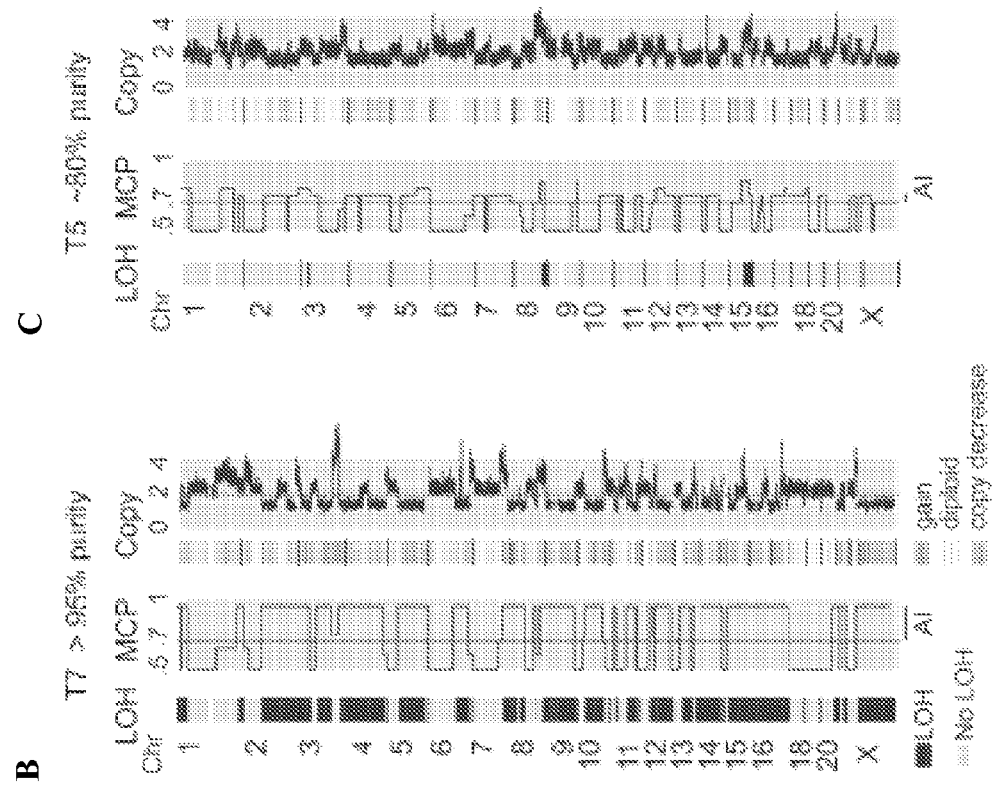
FIGS. 2A-2C show that major copy proportion (MCP) analysis identifies allelic imbalance in tumor biopsy samples with different degrees of tumor cell purity.

Total Number of Chromosomal Rearrangements is Predictive of Chemotherapeutic Drug Sensitivity Without being bound by theory, it is believed that intra-chromosomal loss of heterozycosity (LOH) or allelic imbalance (AI) results from improper repair of chromosomal DNA double-strand breaks and that the genome-wide count of these chromosomal rearrangements in a specific tumor may indicate the degree of DNA repair incompetence, independent of the specific causative DNA repair defect. Therefore, the total number of chromosomal rearrangements in a tumor reflects the inability to repair DNA damage induced by drugs like cisplatin, and consequently predicts sensitivity to these agents. Cisplatin sensitivity of six TNBC cell lines for which SNP array data was available from Wellcome Trust Sanger Institute, UK, was thus determined (FIG. 1A). AI was determined by major copy proportion (MCP) analysis, a method less sensitive to normal contamination in heterogeneous tumor samples (Li et al. (2008) *Bioinformatics* 9, 204). The MCP is the number of major copy alleles at a locus divided by the sum of the number of major plus minor copy alleles (FIG. 2). Gains or reductions in total DNA copy number at each chromosomal region were inferred using dChip software (Lin et al. (2004) *Bioinformatics* 20, 1233-1240).

The DNA repair lesion(s) rendering cells sensitive to cisplatin may preferentially induce chromosomal alterations of a specific type or with a specific size range. In the six cell lines, the association between cisplatin sensitivity and each of four measures of chromosomal alterations was tested. The four measures were (1) the number of chromosome regions with AI ($N_{AI}$), (2) the number of copy number aberrations ($N_{CNA}$), (3) the number of regions with copy number gain, and (4) the number of regions with copy number decrease (FIG. 3). Of these four measures, the $N_{AI}$ was most strongly correlated with cisplatin sensitivity ($R^2$=0.5).

Figure 4:
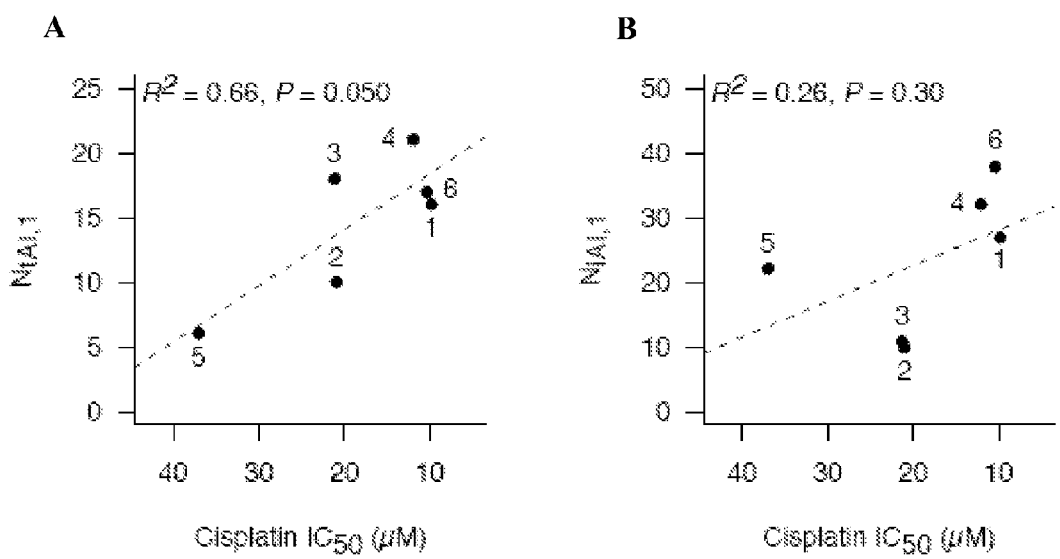
FIGS. 4A-4B show the association between cisplatin sensitivity and count of either telomeric or interstitial AI regions in a panel of TNBC cell lines.

Known defects in DNA double strand break repair, including loss of BRCA1 or mutations in the Bloom helicase, cause the spontaneous formation of triradial and quadriradial chromosome structures, which are cytologic indications of aberrant recombination (Silver et al. (2007) *Cell* 128, 991-1002; Luo et al. (2000)*Nat. Genet.* 26, 424-429; Xu et al. (1999)*Mol. Cell* 3, 389-395). The resolution of these chromosome rearrangements at mitosis can result in loss of distal (telomeric) chromosome fragments and large regions of AI (Luo et al. (2000) *Nat. Genet.* 26, 424-429; Vrieling (2001) *Nat. Genet.* 28, 101-102). Thus, telomeric and interstitial (non-telomeric) AI regions were compared and it was found that the correlation between cisplatin sensitivity and AI was stronger when limited to AI regions involving telomeres, whereas only weak association was seen between cisplatin sensitivity and the number of interstitial AI regions (FIG. 4).

Next, it was determined if the correlations could be improved between cisplatin sensitivity and measures of genomic aberrations by testing a range of minimum segment sizes, in TNBC cell lines (FIG. 1B and FIGS. 5A-5C). Significant correlation with cisplatin sensitivity was seen using minimum telomeric AI segment size cutoffs between 5 and 25 Mb with the highest level of correlation seen for total number of segments with telomeric AI ($N_{tAI}$) of at least 12 MB ($R^2$=0.8; P=0.016; FIG. 1C). Testing for optimum minimum segment size did not appreciably improve the correlation between cisplatin sensitivity and measures of copy number aberrations, which remained not significant (FIGS. 5D-5F).

Whether the same association between $N_{tAI}$ and cisplatin sensitivity was present in clinical tumor samples using the optimum segment size cutoff of 12 MB ($N_{tAI,12}$) was also investigated. $N_{tAI,12}$ was compared to chemotherapy response in subjects with TNBC treated with preoperative cisplatin monotherapy (Silver et al. (2010) *J. Clin. Oncol.* 28, 1145-1153). Cryostat tissue sections of pre-treatment core biopsies were enriched for tumor cells by needle microdissection, and DNA was extracted for genotyping. Genotypes of 42,000 SNPs were determined with the Molecular Inversion Probe (MIP) targeted genotyping system (Affymetrix, Inc.) (Wang et al. (2007) *Genome Biol.* 8, R246). The degree of normal cell contamination was estimated from the MIP genotype data as described (FIG. 2B; Li et al. (2008) *Bioinformatics* 9, 204). No association was observed between the degree of normal contamination and response to cisplatin ($R^2$=0.004, P=0.75).

Figure 6:
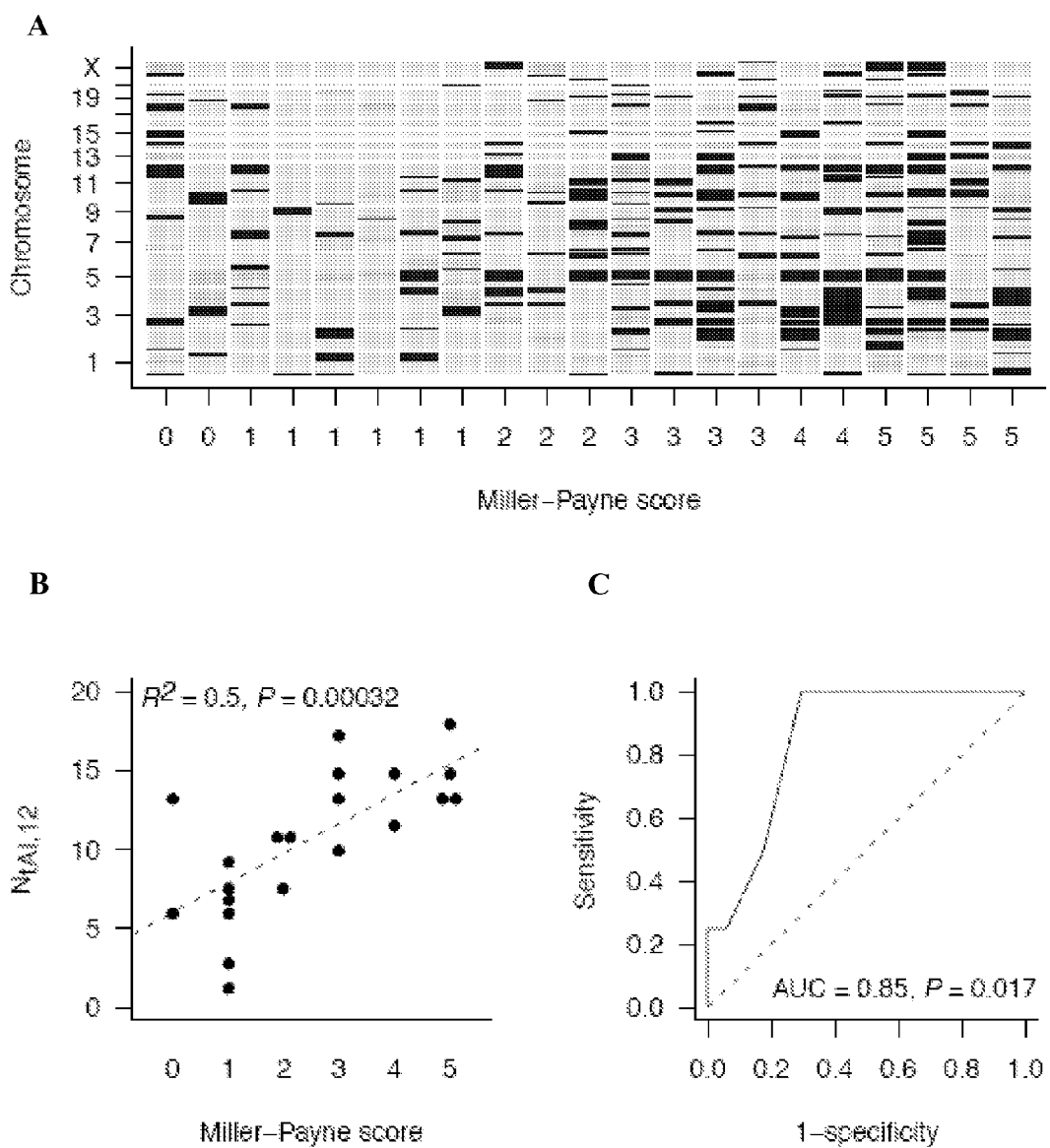
FIGS. 6A-6C show AI regions and cisplatin response in breast cancer. Pathologic response to cisplatin was assessed by the Miller-Payne (MP) score, which can range from 0 (progression) to 5 (pathologic complete response, pCR).
Figure 7:
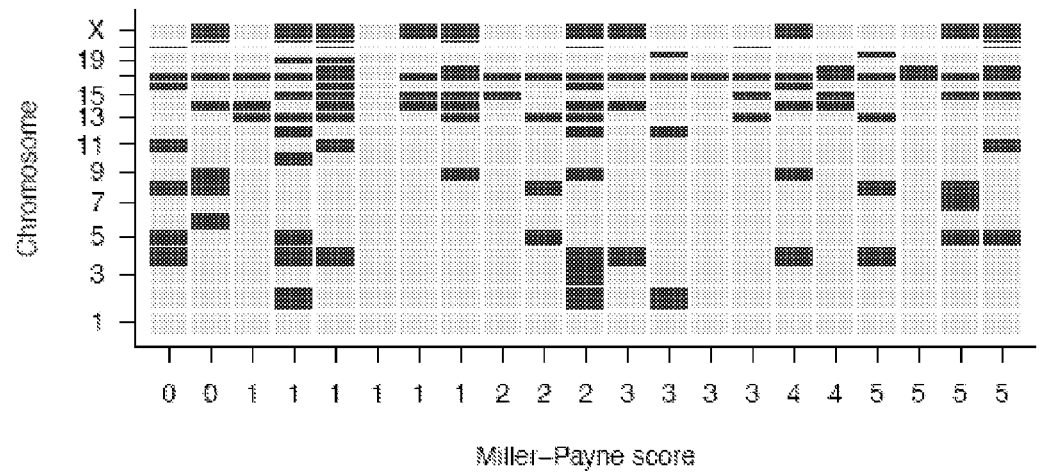
FIG. 7 shows whole chromosome allelic imbalance (isodisomy) and cisplatin sensitivity in breast cancers. Regions of whole chromosome AI are indicated in red for each chromosomal location. Each row defined by thin white lines represents a different chromosome and chromosome numbers are indicated along the left side. Each column represents an individual tumor sample. The Miller-Payne (MP) pathologic response score for each tumor is indicated along the bottom. Cases are arranged in order of increasing pathologic response to cisplatin (0=progression, 5=pathologic complete response (pCR)).

MIP genotype data from 21 cases with at least 75% tumor cell content were evaluated by MCP analysis to define the regions of telomeric, interstitial, or whole chromosome AI across the genome (FIG. 6A and FIG. 7). A correlation between the $N_{tAI,12}$ and the response rate was observed, as quantified by the Miller-Payne score ($R^2$=0.5; P32 0.00032; FIG. 6B; Ogston et al. (2003) *Breast* 12, 320-327), with higher numbers of tAI regions associated with greater sensitivity to cisplatin. Receiver operating characteristic (ROC) curve analysis revealed that $_{NtAI,12}$ was significantly associated with pathologic complete response to cisplatin (Miller-Payne 5) by the area under the curve (AUC=0.85; P=0.017; FIG. 6C). There was no apparent association between number of interstitial AI segments (FIG. 6A) or level of whole chromosome AI (FIG. 7) and response to cisplatin.

Figure 8:
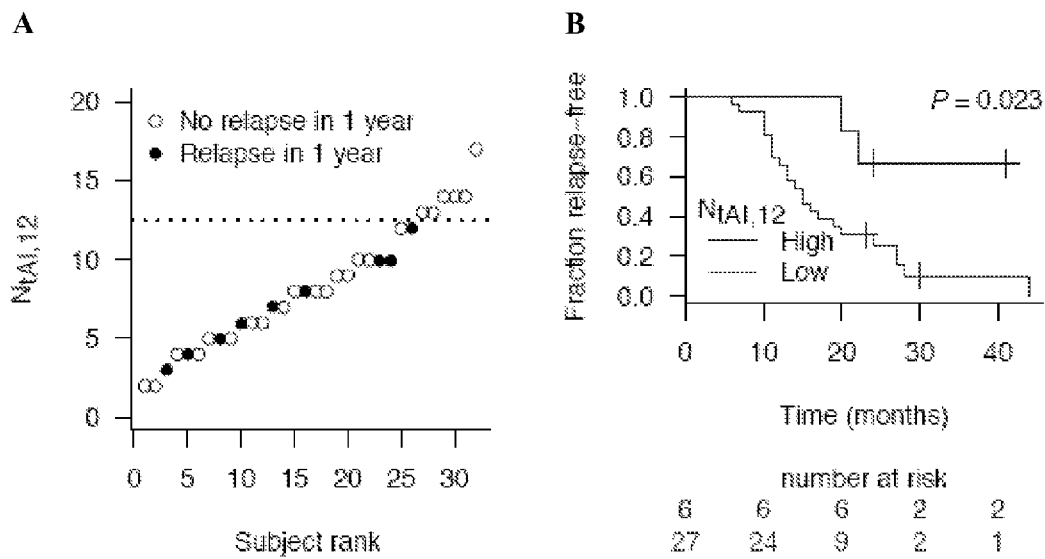
FIGS. 8A-8B show AI regions and time to relapse in serous ovarian cancer treated with platinum based therapy.

Serous ovarian carcinoma is often treated with platinum-based therapies. A publicly available SNP array data set of ovarian carcinomas treated with cisplatin or carboplatin plus a taxane (Etemadmoghadam et al. (2009) *Clin. Cancer Res.* 15, 1417-1427) was investigated and 33 cases of the serous subtype treated after optimal surgical debulking (residual tumor<1 cm) and reasonable tumor purity (>75%, estimated from SNP data) were identified. $N_{tAI,12}$ was determined by MCP analysis. In these platinum-treated ovarian cancer cases, an association was found between higher levels of telomeric AI in tumors and absence of relapse within a year (FIG. 8A). The ROC analysis in the TNBC cohort was used to define a cutoff value of $N_{tAI,12}$ of at least 13 events, which gave the greatest sensitivity for the classification of pCR to platinum therapy in the TNBC cohort. This cutoff was used to classify the ovarian cancer cohort into high and low $N_{tAI,12}$ groups and longer disease-free survival, a surrogate indicator of higher sensitivity to platinum, was found in the high $N_{tAI,12}$ group (FIG. 8B).

Figure 9:
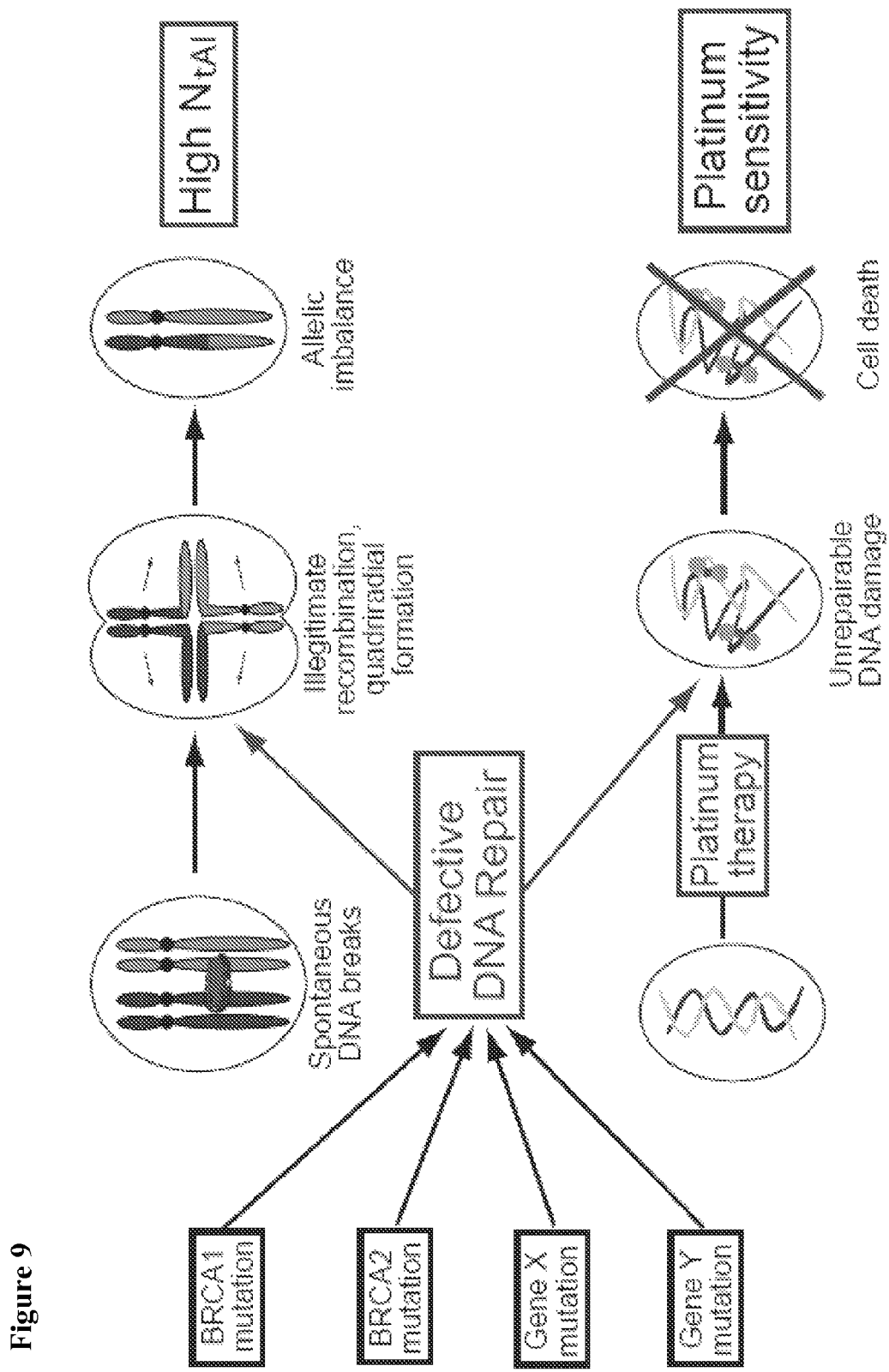
FIG. 9 shows a model relating DNA repair to accumulation of AI and response to platinum agents. Various genetic lesions can result in defects in common pathways of DNA repair, leading first to abnormal repair of spontaneous DNA breaks, then to illegitimate chromosome recombination and aberrant quadriradial chromosome formation, and finally to high levels of telomeric allelic imbalance. In parallel, the defective DNA repair pathway can also result in the inability of the tumor cell to repair drug-induced DNA damage, leading to tumor sensitivity to drugs such as platinum salts. Thus, the level of telomeric AI in a tumor serves as an indicator of defective DNA repair and predicts sensitivity to treatment with genotoxic agents.

Thus, chromosomal instability, manifested by high levels of telomeric AI, characterize subsets of TNBC and ovarian cancer, and further, higher levels of these changes predict specific therapeutic vulnerabilities. Although sporadic TNBC appear similar to BRCA1-associated breast cancer in the patterns of chromosomal alterations and various other immuno-phenotypes and histological features, the precise molecular defect(s) in maintenance of chromosomal stability in these tumors is unknown. The results of the examples described herein indicate that the burden of chromosome rearrangements resulting from improperly repaired DNA strand breaks are indicators of DNA repair defects that sensitize cells to certain chemotherapies (FIG. 9). As such, levels of allelic imbalance provide an accurate biomarker for predicting tumor sensitivity to treatment with genotoxic agents, irrespective of knowledge of the causative DNA repair lesion.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for administering anti-cancer treatment comprising a platinum-based chemotherapeutic agent to a human patient, the method comprising:
    (1) assaying DNA in or derived from a hyperproliferative cell sample from the patient comprising:
        (a) detecting copy number at a plurality of polymorphic chromosomal loci, wherein the plurality of polymorphic chromosomal loci comprises at least 7,000 polymorphic chromosomal loci and wherein there is at least one polymorphic chromosomal locus located on average every 500 kb within each chromosome; and
        (b) detecting, based on the copy numbers detected in (a), allelic imbalance regions having a minimum segment size of 12 Mb and that extend to and involve the telomere and do not cross the centromere;
    (2) calculating a test global chromosomal aberration score (CCAS) for the hyperproliferative cell sample determined by summing the total number of allelic imbalance regions detected in (1);
    (3) detecting a global chromosomal aberration score of at least 8, and
    (4) administering anti-cancer treatment comprising a platinum-based chemotherapeutic agent to the patient.

2. The method of claim 1, wherein the platinum-based chemotherapeutic agent is selected from the group consisting of cisplatin, carboplatin, oxaliplatin, nedaplatin, and iproplatin.

3. The method of claim 1, wherein the hyperproliferative cell sample is from a patient having a cell hyperproliferative disorder selected from the group consisting of breast cancer, ovarian cancer, transitional cell bladder cancer, bronchogenic lung cancer, thyroid cancer, pancreatic cancer, prostate cancer, uterine cancer, testicular cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, Kaposi's sarcoma, Ewing's tumor, refractory multiple myeloma, and squamous cell carcinomas of the head, neck, cervix, colon cancer, melanoma, and vagina.

4. The method of claim 3, wherein the hyperproliferative cell sample is selected from the group consisting of cells, cell lines, histological slides, frozen core biopsies, paraffin embedded tissues, formalin fixed tissues, biopsies, whole blood, nipple aspirate, serum, plasma, buccal scrape, saliva, cerebrospinal fluid, urine, stool, and bone marrow.

5. The method of claim 3, wherein the hyperproliferative cell sample is enriched for the presence of hyperproliferative cells to at least 75% of the total population of cells.

6. The method of claim 5, wherein the enrichment is performed according to at least one technique selected from the group consisting of needle microdissection, laser microdissection, fluorescence activated cell sorting, and immunological cell sorting.

7. The method of claim 6, wherein an automated machine performs the at least one technique to thereby transform the hyperproliferative cell sample into a purified form enriched for the presence of hyperproliferative cells.

8. The method of claim 1, wherein the hyperproliferative cell sample is obtained before the subject has received adjuvant chemotherapy.

9. The method of claim 1, wherein the hyperproliferative cell sample is obtained after the subject has received adjuvant chemotherapy.

10. The method of claim 1, wherein allelic imbalance is detected in (2) using major copy proportion.

11. The method of claim 10, wherein an allelic imbalance region is detected in (2) when MCP is greater than 0 70.

12. The method of claim 1, wherein the plurality of loci comprises at least 35,000 polymorphic chromosomal loci located on average every 100 kb within each chromosome.

13. The method of claim 1, wherein the plurality of chromosomal loci comprise at least one chromosomal locus on each of the 23 human chromosome pairs.

14. The method of claim 1, wherein the plurality of chromosomal loci comprise at least one chromosomal locus on each arm of each of the 23 human chromosome pairs.

15. The method of claim 14, wherein the plurality of chromosomal loci comprise at least one chromosomal locus on at least one telomere of each of the 23 human chromosome pairs.

16. The method of claim 15, wherein the plurality of chromosomal loci comprise at least one chromosomal locus on each telomere of each of the 23 human chromosome pairs.

17. The method of claim 1, wherein a GCAS of at least 13 is detected.

18. The method of claim 1, wherein the polymorphic chromosomal loci are selected from the group consisting of single nucleotide polymorphisms (SNPs), restriction fragment length polymorphisms (RFLPs), and simple tandem repeats (STRs).

19. The method of claim 1, wherein the polymorphic chromosomal loci are genotyped using at least one technique selected from the group consisting of molecular inversion probe (MIP), single nucleotide polymorphism (SNP) array, in situ hybridization, Southern blotting, transcriptional arrays, array comparative genomic hybridization (aCGH), and next-generation sequencing.

20. The method of claim 1, wherein said DNA is derived from said hyperproliferative cell sample by extracting nuclear DNA from the hyperproliferative cell sample by a technique comprising
  (i) contacting the hyperproliferative cell sample with proteinase K and/or RNase A,
  (ii) performing a phenol/chloroform extraction on the mixture of step (i), and
  (iii) performing an ethanol precipitation on the extracted DNA of step (ii).

\* \* \* \* \*

UNITED STATES PATENT AND TRADEMARK OFFICE
CERTIFICATE OF CORRECTION

PATENT NO. : 9,512,485 B2  
APPLICATION NO. : 13/818425  
DATED : December 6, 2016  
INVENTOR(S) : Andrea L. Richardson et al.

Page 1 of 1

It is certified that error appears in the above-identified patent and that said Letters Patent is hereby corrected as shown below:

In the Specification

Column 1, Lines 18-21, delete:
"This invention was made with government support under Grant No. CA089393097193 awarded by The National Institutes of Health. The government has certain rights in the invention."

And insert the following text:
-- This invention was made with government support under Grant No. P30 CA006516 awarded by The National Institutes of Health. The government has certain rights in the invention. --

Signed and Sealed this
Eighth Day of October, 2019

Andrei Iancu
*Director of the United States Patent and Trademark Office*